US012740859B2

(12) United States Patent
Chang et al.

(10) Patent No.: US 12,740,859 B2
(45) **Date of Patent: *Sep. 22, 2026**

(54) HOLDER AND DEPLOYMENT SYSTEM FOR PROSTHETIC HEART VALVES

(71) Applicant: EDWARDS LIFESCIENCES CORPORATION, Irvine, CA (US)

(72) Inventors: Da-Yu Chang, Irvine, CA (US); Hilda Z. Fann, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 98 days.

This patent is subject to a terminal disclaimer.

(21) Appl. No.: 18/620,465

(22) Filed: Mar. 28, 2024

(65) Prior Publication Data

US 2024/0238086 A1 Jul. 18, 2024

Related U.S. Application Data

(63) Continuation of application No. 17/810,182, filed on Jun. 30, 2022, now Pat. No. 11,980,544, which is a (Continued)

(51) Int. Cl.
*A61F 2/24* (2006.01)

(52) U.S. Cl.
CPC .......... *A61F 2/2418* (2013.01); *A61F 2/2427* (2013.01); *A61F 2/243* (2013.01); (Continued)

(58) Field of Classification Search
CPC ............ A61F 2/2418; A61F 2220/0075; A61F 2220/0016; A61F 2/2409; A61F 2/2412; (Continued)

(56) References Cited

U.S. PATENT DOCUMENTS 3,143,742 A 8/1964 Cromie
3,320,972 A 5/1967 High et al.
(Continued)

FOREIGN PATENT DOCUMENTS

EP 0125393 A1 11/1984
EP 0143246 A2 6/1985
(Continued)

OTHER PUBLICATIONS

International Search Report from corresponding PCT case No. PCT/US2015/028523 dated Aug. 3, 2015.

(Continued)

*Primary Examiner* — Katherine M Shi
(74) *Attorney, Agent, or Firm* — Guy Cumberbatch

(57) ABSTRACT

A holder for a hybrid heart valve prosthesis that can be quickly and easily implanted during a surgical procedure is provided. The hybrid heart valve includes a non-expandable, non-compressible prosthetic valve and a self-expandable anchoring stent, thereby enabling attachment to the annulus without sutures. A first suture connects the holder to the valve and constricts an inflow end of the anchoring stent. A second suture connects the holder to the valve and extends down three holder legs to loop through fabric on the valve. Both sutures may loop over a single cutting well on the holder so that severing the first and second sutures at the single cutting well simultaneously releases the tension in the first suture, permitting the inflow end of the anchoring stent to expand, and disconnects the valve holder from the prosthetic heart valve.

11 Claims, 14 Drawing Sheets

Related U.S. Application Data continuation of application No. 16/429,651, filed on Jun. 3, 2019, now Pat. No. 11,376,122, which is a continuation of application No. 15/451,203, filed on Mar. 6, 2017, now Pat. No. 10,307,249, which is a continuation of application No. 14/700,007, filed on Apr. 29, 2015, now Pat. No. 9,585,752.

(60) Provisional application No. 61/986,761, filed on Apr. 30, 2014.

(52) U.S. Cl.
CPC ........ *A61F 2/2439* (2013.01); *A61F 2210/00* (2013.01); *A61F 2210/0014* (2013.01); *A61F 2220/0075* (2013.01); *A61F 2230/0069* (2013.01)

(58) Field of Classification Search
CPC ...... A61F 2220/0008; A61F 2220/0025; A61F 2/2427; A61F 2/2439; A61F 2/24
See application file for complete search history.

(56) References Cited

U.S. PATENT DOCUMENTS 3,371,352 A 3/1968 Siposs et al.
3,409,013 A 11/1968 Berry
3,546,710 A 12/1970 Shumakov et al.
3,574,865 A 4/1971 Hamaker
3,628,535 A 12/1971 Ostrowsky et al.
3,657,744 A 4/1972 Ersek
3,686,740 A 8/1972 Shiley
3,755,823 A 9/1973 Hancock
3,839,741 A 10/1974 Haller
4,035,849 A 7/1977 Angell et al.
4,078,468 A 3/1978 Civitello
4,079,468 A 3/1978 Liotta et al.
4,084,268 A 4/1978 Ionescu et al.
4,106,129 A 8/1978 Carpentier et al.
4,172,295 A 10/1979 Batten
4,217,665 A 8/1980 Bex et al.
4,218,782 A 8/1980 Rygg
4,259,753 A 4/1981 Liotta et al.
4,340,091 A 7/1982 Skelton et al.
4,343,048 A 8/1982 Ross et al.
4,364,126 A 12/1982 Rosen et al.
4,388,735 A 6/1983 Ionescu et al.
4,441,216 A 4/1984 Ionescu et al.
4,451,936 A 6/1984 Carpentier et al.
4,470,157 A 9/1984 Love
4,490,859 A 1/1985 Black et al.
4,501,030 A 2/1985 Lane
4,506,394 A 3/1985 Bedard
4,535,483 A 8/1985 Klawitter et al.
4,605,407 A 8/1986 Black et al.
4,626,255 A 12/1986 Reichart et al.
4,629,459 A 12/1986 Ionescu et al.
4,680,031 A 7/1987 Alonso
4,687,483 A 8/1987 Fisher et al.
4,702,250 A 10/1987 Ovil et al.
4,705,516 A 11/1987 Barone et al.
4,725,274 A 2/1988 Lane et al.
4,731,074 A 3/1988 Rousseau et al.
4,778,461 A 10/1988 Pietsch et al.
4,790,843 A 12/1988 Carpentier et al.
4,851,000 A 7/1989 Gupta
4,865,600 A 9/1989 Carpentier et al.
4,888,009 A 12/1989 Lederman et al.
4,914,097 A 4/1990 Oda et al.
4,960,424 A 10/1990 Grooters
4,993,428 A 2/1991 Arms
5,010,892 A 4/1991 Colvin et al.
5,032,128 A 7/1991 Alonso
5,037,434 A 8/1991 Lane
5,147,391 A 9/1992 Lane
5,163,955 A 11/1992 Love et al.
5,258,023 A 11/1993 Reger
5,316,016 A 5/1994 Adams et al.
5,326,370 A 7/1994 Love et al.
5,326,371 A 7/1994 Love et al.
5,332,402 A 7/1994 Teitelbaum
5,350,420 A 9/1994 Cosgrove et al.
5,360,444 A 11/1994 Kusuhara
5,370,685 A 12/1994 Stevens
5,376,112 A 12/1994 Duran
5,396,887 A 3/1995 Imran
5,397,351 A 3/1995 Pavcnik et al.
5,411,522 A 5/1995 Trott
5,423,887 A 6/1995 Love et al.
5,425,741 A 6/1995 Lemp et al.
5,431,676 A 7/1995 Dubrul et al.
5,443,502 A 8/1995 Caudillo et al.
5,449,384 A 9/1995 Johnson
5,449,385 A 9/1995 Religa et al.
5,469,868 A 11/1995 Reger
5,476,510 A 12/1995 Eberhardt et al.
5,488,789 A 2/1996 Religa et al.
5,489,297 A 2/1996 Duran
5,489,298 A 2/1996 Love et al.
5,500,016 A 3/1996 Fisher
5,533,515 A 7/1996 Coller et al.
5,549,665 A 8/1996 Vesely et al.
5,562,729 A 10/1996 Purdy et al.
5,571,215 A 11/1996 Sterman et al.
5,573,007 A 11/1996 Bobo, Sr.
5,578,076 A 11/1996 Krueger et al.
5,584,803 A 12/1996 Stevens et al.
5,618,307 A 4/1997 Donlon et al.
5,626,607 A 5/1997 Malecki et al.
5,628,789 A 5/1997 Vanney et al.
5,693,090 A 12/1997 Unsworth et al.
5,695,503 A 12/1997 Krueger et al.
5,713,952 A 2/1998 Vanney et al.
5,716,370 A 2/1998 Williamson, IV et al.
5,728,064 A 3/1998 Burns et al.
5,728,151 A 3/1998 Garrison et al.
5,735,894 A 4/1998 Krueger et al.
5,752,522 A 5/1998 Murphy
5,755,782 A 5/1998 Love et al.
5,766,240 A 6/1998 Johnson
5,776,187 A 7/1998 Krueger et al.
5,776,188 A 7/1998 Shepherd et al.
5,800,527 A 9/1998 Jansen et al.
5,814,097 A 9/1998 Sterman et al.
5,814,098 A 9/1998 Hinnenkamp et al.
5,824,064 A 10/1998 Taheri
5,824,068 A 10/1998 Bugge
5,840,081 A 11/1998 Andersen et al.
5,848,969 A 12/1998 Panescu et al.
5,855,563 A 1/1999 Kaplan et al.
5,855,601 A 1/1999 Bessler et al.
5,865,801 A 2/1999 Houser
5,891,160 A 4/1999 Williamson, IV et al.
5,895,420 A 4/1999 Mirsch, II et al.
5,902,308 A 5/1999 Murphy
5,908,450 A 6/1999 Gross et al.
5,919,147 A 7/1999 Jain
5,921,934 A 7/1999 Teo
5,921,935 A 7/1999 Hickey
5,924,984 A 7/1999 Rao
5,928,281 A 7/1999 Huynh et al.
5,957,949 A 9/1999 Leonhardt et al.
5,972,004 A 10/1999 Williamson, IV et al.
5,984,959 A 11/1999 Robertson et al.
5,984,973 A 11/1999 Girard et al.
6,010,531 A 1/2000 Donlon et al.
6,042,607 A 3/2000 Williamson, IV et al.
6,059,827 A 5/2000 Fenton, Jr.
6,066,160 A 5/2000 Colvin et al.
6,074,418 A 6/2000 Buchanan et al.
6,081,737 A 6/2000 Shah
6,083,179 A 7/2000 Oredsson
6,099,475 A 8/2000 Seward et al.

(56) References Cited

U.S. PATENT DOCUMENTS 6,106,550 A 8/2000 Magovern et al.
6,110,200 A 8/2000 Hinnenkamp
6,117,091 A 9/2000 Young et al.
6,126,007 A 10/2000 Kari et al.
6,264,611 B1 7/2001 Ishikawa et al.
6,319,280 B1 11/2001 Schoon
6,322,526 B1 11/2001 Rosenman et al.
6,350,282 B1 2/2002 Eberhardt
6,491,624 B1 12/2002 Lotfi
6,773,457 B2 8/2004 Ivancev et al.
7,018,404 B2 3/2006 Holmberg et al.
7,037,333 B2 5/2006 Myers et al.
7,189,258 B2 3/2007 Johnson et al.
7,998,151 B2 8/2011 St. Goar et al.
8,152,844 B2 4/2012 Rao et al.
8,308,798 B2 11/2012 Pintor et al.
8,323,337 B2 12/2012 Gurskis et al.
8,348,998 B2 1/2013 Pintor et al.
2001/0021872 A1 9/2001 Bailey et al.
2001/0039435 A1 11/2001 Roue et al.
2001/0039436 A1 11/2001 Frazier et al.
2001/0041914 A1 11/2001 Frazier et al.
2001/0041915 A1 11/2001 Roue et al.
2001/0049492 A1 12/2001 Frazier et al.
2002/0026238 A1 2/2002 Lane et al.
2002/0032481 A1 3/2002 Gabbay
2002/0058995 A1 5/2002 Stevens
2002/0123802 A1 9/2002 Snyders
2002/0133226 A1 9/2002 Marquez et al.
2002/0138138 A1 9/2002 Yang
2002/0151970 A1 10/2002 Garrison et al.
2002/0188348 A1 12/2002 DiMatteo et al.
2002/0198594 A1 12/2002 Schreck
2003/0014104 A1 1/2003 Cribier
2003/0023300 A1 1/2003 Bailey et al.
2003/0023303 A1 1/2003 Palmaz et al.
2003/0036795 A1 2/2003 Andersen et al.
2003/0040792 A1 2/2003 Gabbay
2003/0055495 A1 3/2003 Pease et al.
2003/0105519 A1 6/2003 Fasol et al.
2003/0109924 A1 6/2003 Cribier
2003/0114913 A1 6/2003 Spenser et al.
2003/0130729 A1 7/2003 Paniagua et al.
2003/0149478 A1 8/2003 Figulla et al.
2003/0167089 A1 9/2003 Lane
2003/0236568 A1 12/2003 Hojeibane et al.
2004/0019374 A1 1/2004 Hojeibane et al.
2004/0034411 A1 2/2004 Quijano et al.
2004/0044406 A1 3/2004 Woolfson et al.
2004/0106976 A1 6/2004 Bailey et al.
2004/0122514 A1 6/2004 Fogarty et al.
2004/0122516 A1 6/2004 Fogarty et al.
2004/0167573 A1 8/2004 Williamson et al.
2004/0186563 A1 9/2004 Lobbi
2004/0186565 A1 9/2004 Schreck
2004/0193261 A1 9/2004 Berreklouw
2004/0206363 A1 10/2004 McCarthy et al.
2004/0210304 A1 10/2004 Seguin et al.
2004/0210305 A1 10/2004 Shu et al.
2004/0210307 A1 10/2004 Khairkhahan
2004/0225355 A1 11/2004 Stevens
2004/0236411 A1 11/2004 Sarac et al.
2004/0260389 A1 12/2004 Case et al.
2004/0260390 A1 12/2004 Sarac et al.
2005/0010285 A1 1/2005 Lambrecht et al.
2005/0027348 A1 2/2005 Case et al.
2005/0033398 A1 2/2005 Seguin
2005/0043760 A1 2/2005 Fogarty et al.
2005/0043790 A1 2/2005 Seguin
2005/0060029 A1 3/2005 Le et al.
2005/0065594 A1 3/2005 DiMatteo et al.
2005/0065614 A1 3/2005 Stinson
2005/0075584 A1 4/2005 Cali
2005/0075713 A1 4/2005 Biancucci et al.
2005/0075717 A1 4/2005 Nguyen et al.
2005/0075718 A1 4/2005 Nguyen et al.
2005/0075719 A1 4/2005 Bergheim
2005/0075720 A1 4/2005 Nguyen et al.
2005/0075724 A1 4/2005 Svanidze et al.
2005/0080454 A1 4/2005 Drews et al.
2005/0096738 A1 5/2005 Cali et al.
2005/0137682 A1 6/2005 Justino
2005/0137686 A1 6/2005 Salahieh et al.
2005/0137687 A1 6/2005 Salahieh et al.
2005/0137688 A1 6/2005 Salahieh et al.
2005/0137689 A1 6/2005 Salahieh et al.
2005/0137690 A1 6/2005 Salahieh et al.
2005/0137691 A1 6/2005 Salahieh et al.
2005/0137692 A1 6/2005 Haug et al.
2005/0137694 A1 6/2005 Haug et al.
2005/0137695 A1 6/2005 Salahieh et al.
2005/0137702 A1 6/2005 Haug et al.
2005/0159811 A1 7/2005 Lane
2005/0165477 A1 7/2005 Anduiza et al.
2005/0165479 A1 7/2005 Drews et al.
2005/0182483 A1 8/2005 Osborne et al.
2005/0182486 A1 8/2005 Gabbay
2005/0192665 A1 9/2005 Spenser et al.
2005/0203616 A1 9/2005 Cribier
2005/0203617 A1 9/2005 Forster et al.
2005/0203618 A1 9/2005 Sharkawy et al.
2005/0216079 A1 9/2005 MaCoviak
2005/0222674 A1 10/2005 Paine
2005/0234546 A1 10/2005 Nugent et al.
2005/0240259 A1 10/2005 Sisken et al.
2005/0251252 A1 11/2005 Stobie
2005/0261765 A1 11/2005 Liddicoat
2005/0283231 A1 12/2005 Haug et al.
2006/0025857 A1 2/2006 Bergheim et al.
2006/0052867 A1 3/2006 Revuelta et al.
2006/0058871 A1 3/2006 Zakay et al.
2006/0058872 A1 3/2006 Salahieh et al.
2006/0074484 A1 4/2006 Huber
2006/0085060 A1 4/2006 Campbell
2006/0095125 A1 5/2006 Chinn et al.
2006/0122634 A1 6/2006 Ino et al.
2006/0122692 A1 6/2006 Gilad et al.
2006/0136054 A1 6/2006 Berg et al.
2006/0149360 A1 7/2006 Schwammenthal et al.
2006/0154230 A1 7/2006 Cunanan et al.
2006/0161249 A1 7/2006 Realyvasquez et al.
2006/0167543 A1 7/2006 Bailey et al.
2006/0195183 A1 8/2006 Navia et al.
2006/0195184 A1 8/2006 Lane et al.
2006/0195185 A1 8/2006 Lane et al.
2006/0195186 A1 8/2006 Drews et al.
2006/0207031 A1 9/2006 Cunanan et al.
2006/0229708 A1 10/2006 Powell et al.
2006/0235508 A1 10/2006 Lane et al.
2006/0241745 A1 10/2006 Solem
2006/0246888 A1 11/2006 Bender et al.
2006/0253191 A1 11/2006 Salahieh et al.
2006/0259134 A1 11/2006 Schwammenthal et al.
2006/0259135 A1 11/2006 Navia et al.
2006/0259136 A1 11/2006 Nguyen et al.
2006/0265056 A1 11/2006 Nguyen et al.
2006/0271172 A1 11/2006 Tehrani
2006/0271175 A1 11/2006 Woolfson et al.
2006/0287717 A1 12/2006 Rowe et al.
2006/0287719 A1 12/2006 Rowe et al.
2006/0293745 A1 12/2006 Carpentier et al.
2007/0005129 A1 1/2007 Damm et al.
2007/0010876 A1 1/2007 Salahieh et al.
2007/0010877 A1 1/2007 Salahieh et al.
2007/0016285 A1 1/2007 Lane et al.
2007/0016286 A1 1/2007 Herrmann et al.
2007/0016288 A1 1/2007 Gurskis et al.
2007/0043435 A1 2/2007 Seguin et al.
2007/0078509 A1 4/2007 Lotfy
2007/0078510 A1 4/2007 Ryan
2007/0100440 A1 5/2007 Figulla et al.
2007/0129794 A1 6/2007 Realyvasquez
2007/0142906 A1 6/2007 Figulla et al.
2007/0142907 A1 6/2007 Moaddeb et al.

(56) References Cited

U.S. PATENT DOCUMENTS

2007/0150053 A1 6/2007 Gurskis et al.
2007/0156233 A1 7/2007 Kapadia et al.
2007/0162103 A1 7/2007 Case et al.
2007/0162107 A1 7/2007 Haug et al.
2007/0162111 A1 7/2007 Fukamachi et al.
2007/0179604 A1 8/2007 Lane
2007/0185565 A1 8/2007 Schwammenthal et al.
2007/0198097 A1 8/2007 Zegdi
2007/0203575 A1 8/2007 Forster et al.
2007/0203576 A1 8/2007 Lee et al.
2007/0213813 A1 9/2007 Von Segesser et al.
2007/0225801 A1 9/2007 Drews et al.
2007/0233237 A1 10/2007 Krivoruchko
2007/0239266 A1 10/2007 Birdsall
2007/0239269 A1 10/2007 Dolan et al.
2007/0239273 A1 10/2007 Allen
2007/0244546 A1 10/2007 Francis
2007/0244558 A1 10/2007 Machiraju
2007/0255398 A1 11/2007 Yang et al.
2007/0260305 A1 11/2007 Drews et al.
2007/0265701 A1 11/2007 Gurskis et al.
2007/0270944 A1 11/2007 Bergheim et al.
2007/0282436 A1 12/2007 Pinchuk
2007/0288089 A1 12/2007 Gurskis et al.
2008/0021546 A1 1/2008 Patz et al.
2008/0033543 A1 2/2008 Gurskis et al.
2008/0065198 A1 3/2008 Quintessenza
2008/0119875 A1 5/2008 Ino et al.
2008/0154356 A1 6/2008 Obermiller et al.
2008/0281411 A1 11/2008 Berreklouw
2008/0319543 A1 12/2008 Lane
2009/0036903 A1 2/2009 Ino et al.
2009/0192599 A1 7/2009 Lane et al.
2009/0192602 A1 7/2009 Kuehn
2009/0192603 A1 7/2009 Kuehn
2009/0192604 A1 7/2009 Gloss
2009/0192605 A1 7/2009 Gloss et al.
2009/0192606 A1 7/2009 Gloss et al.
2009/0299470 A1* 12/2009 Rao ...................... A61F 2/2466 623/2.36
2010/0161036 A1 6/2010 Pintor et al.
2010/0249894 A1 9/2010 Oba et al.
2010/0249908 A1 9/2010 Chau et al.
2010/0331972 A1 12/2010 Pintor et al.
2011/0022165 A1 1/2011 Oba et al.
2011/0147251 A1 6/2011 Hodshon et al.
2012/0065729 A1 3/2012 Pintor et al.
2012/0078357 A1 3/2012 Conklin
2012/0150288 A1 6/2012 Hodshon et al.
2012/0323317 A1 12/2012 Karapetian et al.
2013/0053949 A1 2/2013 Pintor et al.
2013/0116777 A1 5/2013 Pintor et al.

FOREIGN PATENT DOCUMENTS

SU 1116573 A1 7/1985
SU 1697790 A1 12/1991
WO 9213502 A1 8/1992
WO 9742871 A1 11/1997

OTHER PUBLICATIONS

Krakow, "3F Therapeutics, Inc. Announces the First Clinical Implantation of the 3F Enable Aortic Heart Valve.TM., a Patented, Sutureless Implantation, Replacement Heart Valve Intended to Save Valuable Surgery Time and Reduce Time RelatedComplications . . . " Healthcare Sales & Marketing Network News Feed, Jan. 18, 2005, pp. 1-2. cited by other.

Sadowski, Jerzy; Kapelak, Boguslaw; Bartus, Krzysztof, "Sutureless Heart Valve Implantation—A Case Study," Touch Briefings, 2005, pp. 48-50. cited by other.

* cited by examiner 22
30
32
34
36
40
24
42
20

HOLDER AND DEPLOYMENT SYSTEM FOR PROSTHETIC HEART VALVES

CROSS-REFERENCE TO RELATED APPLICATIONS

This application is a continuation of U.S. patent application Ser. No. 17/810,182, filed Jun. 30, 2022, which is a continuation of U.S. patent application Ser. No. 16/429,651, filed Jun. 3, 2019, which is a continuation of U.S. patent application Ser. No. 15/451,203, filed Mar. 6, 2017, now U.S. Pat. No. 10,307,249, which is a continuation of U.S. patent application Ser. No. 14/700,007, filed Apr. 29, 2015, now U.S. Pat. No. 9,585,752, which claims the benefit of U.S. Patent Application No. 61/986,761, filed Apr. 30, 2014, the entire disclosures all of which are incorporated by reference for all purposes.

TECHNICAL FIELD

The present application generally relates to prosthetic valves for implantation in body channels. More particularly, the present application relates to a holder for a hybrid surgical prosthetic heart valve having a non-collapsible/non-expandable valve portion and a self-expanding anchoring stent.

BACKGROUND

In vertebrate animals, the heart is a hollow muscular organ having four pumping chambers—the left and right atria and the left and right ventricles—each provided with its own one-way valve to ensure that blood does not flow in the wrong direction. The mitral valve is between the left atrium and the left ventricle, the tricuspid valve between the right atrium and the right ventricle, the pulmonary valve is at the opening of the pulmonary artery, and the aortic valve is at the opening of the aorta above the left ventricle. The natural heart valves are each mounted in an annulus comprising dense fibrous rings attached either directly or indirectly to the atrial and ventricular muscle fibers. Each annulus defines a flow orifice.

Various surgical techniques may be used to repair or replace a diseased or damaged valve. Due to aortic stenosis and other heart valve diseases, thousands of patients undergo surgery each year wherein the defective native heart valve is replaced by a prosthetic valve, either bioprosthetic or mechanical.

When the valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. Due to these risks, a substantial number of patients with defective valves are deemed inoperable because their condition is too frail to withstand the procedure. By some estimates, about 30 to 50% of the subjects suffering from aortic stenosis who are older than 80 years cannot be operated on for aortic valve replacement.

Percutaneous and minimally-invasive surgical approaches, some of which avoid cardiopulmonary bypass altogether in "beating heart" procedures, are garnering intense attention. Although these remote implantation techniques have shown great promise for treating certain patients, replacing a valve via surgical intervention and bypass is still the preferred treatment procedure. One hurdle to the acceptance of remote implantation is resistance from doctors who are anxious about converting from an effective, if imperfect, regimen to a novel approach that promises great outcomes but is relatively foreign. In conjunction with the understandable caution exercised by surgeons in switching to new techniques of heart valve replacement, regulatory bodies around the world are moving slowly as well.

Accordingly, there is a need for a prosthetic valve that can be surgically implanted in a body channel in a more efficient procedure so as to reduce the time required on extracorporeal circulation. One solution especially for aortic valve replacement is provided by the Edwards Intuity valve system available from Edwards Lifesciences of Irvine, CA. Aspects of the Edwards Intuity valve system are disclosed in U.S. Pat. No. 8,641,757 to Pintor, et al. The Edwards Intuity valve is a hybrid of a surgical valve and an expandable stent that helps secure the valve in place in a shorter amount of time. The implant process only requires three sutures which reduces the time-consuming process of tying knots. A delivery system advances the Edwards Intuity valve with the stent at the leading end until it is located within the left ventricle, at which point a balloon inflates to expand the stent against the ventricular wall. The long handle and delivery system design facilitate access through smaller incisions (mini-sternotomy or right anterior thoracotomy) than with conventional full sternotomies.

There remains a need for further innovative approaches like the Edwards Intuity valve system that combine the proven effectiveness of existing surgical valves and shorten the implant procedure time.

SUMMARY

The present application discloses prosthetic valves and methods of use for replacing a defective native valve in a human heart. Certain embodiments are particularly well adapted for use in a surgical procedure for quickly and easily replacing a heart valve while minimizing time using extracorporeal circulation (e.g., bypass pump). In particular, the application discloses an advantageous system and method for holding and delivering a hybrid prosthetic heart in less time than previously was possible.

One aspect of the application is a combination of a prosthetic heart valve for implant at a heart valve annulus and a holder therefor. The combination includes a "hybrid" prosthetic heart valve having a valve member and a self-expandable anchoring stent. The valve member includes a non-expandable, non-collapsible annular support structure defining a flow orifice and an inflow end defining an inflow direction with an outflow direction opposite thereto. The valve member also has valve leaflets attached to the support structure and mounted to alternately open and close across the flow orifice. The self-expandable anchoring stent has a first or outflow end extending around the flow orifice and connected to the valve member at the inflow end of the support structure so that the first end maintains a fixed diameter. The anchoring stent also has a second or inflow end projecting in the inflow direction away from the support structure and having a relaxed, expanded shape defining a first peripheral size.

In a first embodiment, the valve holder connects by a first suture to the prosthetic heart valve, wherein the first suture extends around the second end of the anchoring stent and is placed under tension to constrict the second end to a second peripheral size smaller than the first peripheral size. The first suture desirably passes over a single cutting well on the valve holder such that severing the first suture at the single cutting well releases the tension therein and permits the second end of the anchoring stent to expand toward its first peripheral size.

In a second embodiment, the valve holder connects by a first suture to the prosthetic heart valve, wherein the first suture has a first free end attached to the valve holder, a middle portion that extends in a first length in the inflow direction, in a second length around the entire inflow end of the anchoring stent, and in a third length back to the valve holder alongside the first length, the first suture further having a fourth length that passes over a cutting well on the valve holder and ends in a second free end attached to the valve holder such that when the two free ends are attached to the valve holder the first suture is under tension and constricts the inflow end from a relaxed size to a smaller size.

In either valve-holder connection embodiment, the anchoring stent has a fabric covering, and wherein the first suture passes in a serpentine fashion through the fabric covering around the second or inflow end of the anchoring stent. The valve holders may be further connected by a second suture to the prosthetic heart valves, each valve holder including a plurality of legs (preferably three) that contact the valve member at the same number of locations having fabric incorporated into the valve member, and wherein the second suture passes circumferentially around the valve holder and threads through the fabric at the locations. Both the first and second sutures desirably pass over a single cutting well on the valve holder such that severing the first and second sutures at the single cutting well simultaneously releases the tension in the first suture, permitting the second end of the anchoring stent to expand toward its first peripheral size, and disconnects the valve holder from the prosthetic heart valve. The valve member support structure preferably has three commissure posts projecting in the outflow direction and three cusps therebetween that arc in the inflow direction, and the valve leaflets are flexible and partly supported by the commissure posts of the support structure. In this configuration, the valve holder includes a central hub and three legs that angle outward and in the inflow direction to contact the valve member at the three cusps, and wherein the first suture is tied at two free ends to a terminal foot of one of the holder legs. Also with this valve configuration, the valve holders further may be connected by a second suture to the prosthetic heart valve that passes circumferentially around the valve holder and threads through the fabric at the three cusps. The second suture may be tied at first and second free ends to the holder, and in between passes circumferentially around the hub of the holder and descends down each of the three legs to pass through two holes at a terminal foot thereof. The second suture is also preferably threaded through the fabric at each of the three cusps between the two holes, and circles completely around each leg between the hub and the respective foot.

A method of deploying a prosthetic heart valve for implant at a heart valve annulus disclosed herein comprises:

providing a prosthetic heart valve having a valve member with a non-expandable, non-collapsible annular support structure and valve leaflets mounted thereto to alternately open and close, and a self-expandable anchoring stent connected to the valve member at an inflow end of the support structure and having an inflow end projecting in the inflow direction away from the support structure, the prosthetic heart valve being secured to a valve holder by a first suture that attaches at two free ends to the valve holder and extends around the entire inflow end of the anchoring stent under tension and constricts the inflow end from a relaxed size to a smaller size, the first suture having a middle portion that passes over a cutting well on the valve holder;

advancing the prosthetic heart valve to the heart valve annulus; and severing the first suture at the cutting well to release the tension therein and permit the inflow end of the anchoring stent to expand toward its relaxed size.

The method may also involve a second suture connecting the prosthetic heart valve to the holder, wherein both the first and second sutures pass over the cutting well on the valve holder such that severing the first and second sutures at the cutting well simultaneously releases the tension in the first suture, permitting the inflow end of the anchoring stent to expand toward its first peripheral size, and disconnects the valve holder from the prosthetic heart valve. The valve holder preferably includes a central hub and a plurality of legs that contact the valve member at the same number of locations having fabric incorporated into the valve member, wherein the second suture passes circumferentially around the valve holder and threads through the fabric at the locations. The second suture is desirably tied at first and second free ends to the holder, and in between passes circumferentially around the hub of the holder and descends down each of the legs to pass through two holes at a terminal foot thereof. The valve member support structure preferably has three commissure posts projecting in the outflow direction and three cusps therebetween that arc in the inflow direction, and the second suture is threaded through the fabric at each of the three cusps and between the two holes, and wherein the second suture circles completely around each leg between the hub and the respective foot.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIGS. 6-11B illustrate a number of steps taken to couple the valve holder to the heart valve using an upper connecting suture, wherein:

FIG. 6 shows the valve holder exploded above the heart valve and the initial path of the upper connecting suture passed downward through a portion of the fabric of the heart valve;

FIGS. 7A and 7B are perspective and top plan views of the valve holder in contact with the heart valve and illustrating the path of the upper connecting suture after having secured a first leg of the holder to the heart valve;

FIGS. 8A and 8B illustrate the path of the upper connecting suture as it traverses between the first leg of the holder to a second leg where it is again secured to the heart valve;

FIGS. 9A and 9B illustrate the path of the upper connecting suture after having secured the second leg of the holder to the heart valve and wraps around a cutting well provided on the second leg of the holder;

FIGS. 10A and 10B illustrate the path of the upper connecting suture as it traverses between the second leg of the holder to a third leg where it is again secured to the heart valve;

FIGS. 11A and 11B illustrate a second free end of the upper connecting suture after being secured to the holder at the first leg;

FIGS. 12A-13B illustrate a number of steps taken to further couple the valve holder to the heart valve and constrict the anchoring stent using a lower connecting suture, wherein:

FIGS. 12A and 12B are two perspective views of the valve holder secured to the heart valve via the upper connecting suture and illustrating the initial path of the lower connecting suture as it passes downward from the second leg of the holder through fabric of the heart valve to a lower end of the anchoring stent;

FIGS. 13A and 13B illustrate a second free end of the lower connecting suture again secured to the valve holder;

FIGS. 14A and 14B are top and bottom plan views, respectively, of the valve holder secured to the heart valve using the connecting sutures;

DETAILED DESCRIPTION OF CERTAIN EMBODIMENTS

Figures 1, 2, 3:
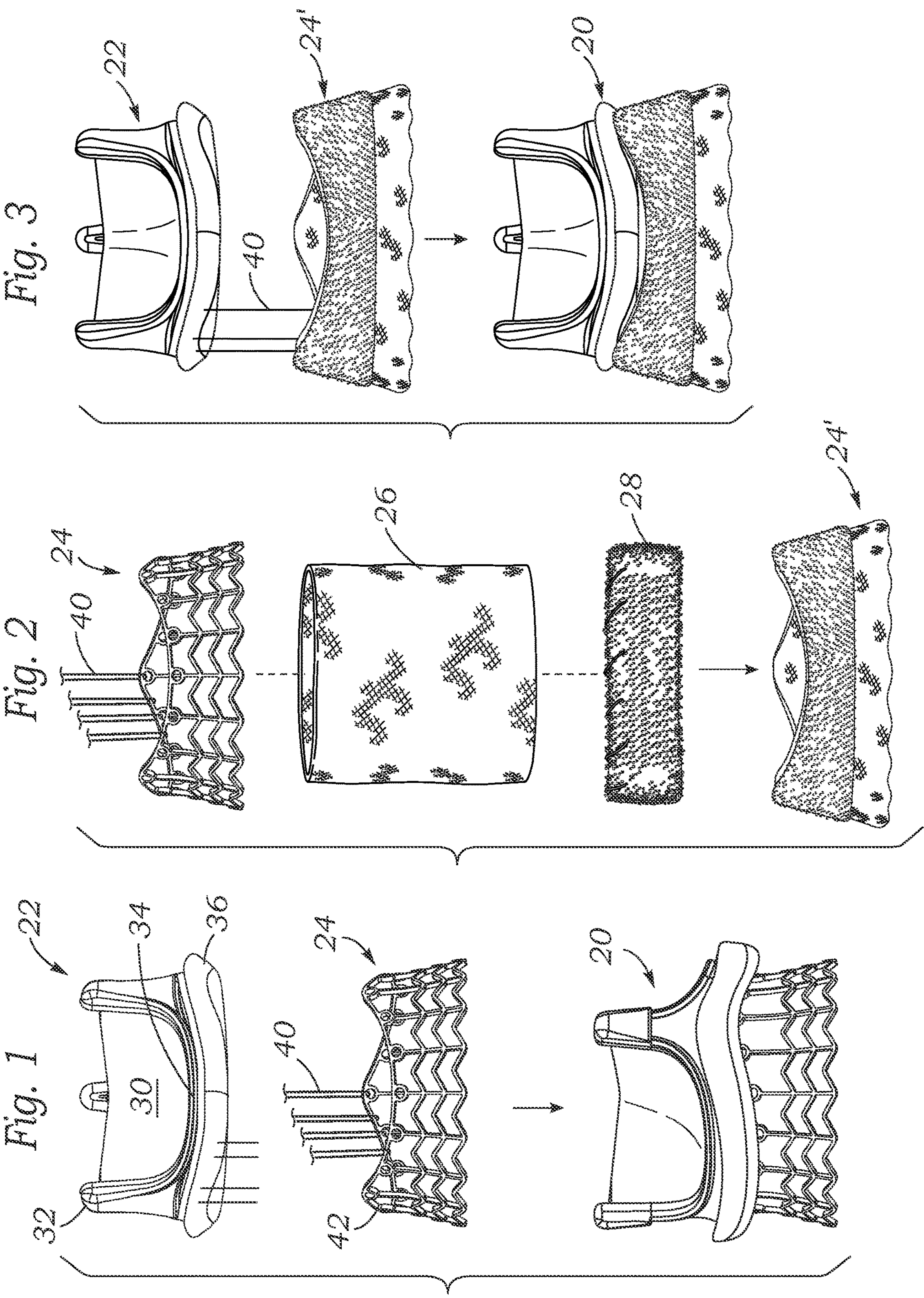
FIG. 1 shows both exploded and assembled views of an exemplary hybrid prosthetic heart valve (hereinafter, "heart valve") for which the holder and deployment system of the present application is designed, with fabric coverings removed from an anchoring stent for clarity.
FIG. 2 is an exploded view of the expandable anchoring stent and its fabric coverings which form a component of the heart valve in FIG. 1.
FIG. 3 shows both exploded and assembled views of the finished heart valve showing the fabric-covered anchoring stent in its expanded, deployed state.

The present disclosure provides a valve holder for hybrid prosthetic heart valves delivered by open-heart surgery, but which include features that decrease the duration of the treatment procedure. The prosthetic heart valves of the present invention are primarily intended to be delivered and implanted using surgical techniques, including the aforementioned open-heart surgery. There are a number of approaches in such surgeries, all of which result in the formation of a direct access pathway to the particular heart valve annulus. For clarification, a direct access pathway is one that permits direct (e.g., naked eye) visualization of the heart valve annulus.

The "hybrid" prosthetic heart valve has both non-expandable and expandable portions; specifically, an expandable anchoring stent or stent coupled to a non-expandable valve member. With this type of valve, the duration of the anchoring operation is greatly reduced as compared with a typical sewing procedure utilizing an array of sutures that must be knotted. The expandable anchoring stent may simply be radially expanded outward into contact with the implantation site, or may be provided with additional anchoring means, such as barbs. As stated, open-heart approach and cardiopulmonary bypass familiar to cardiac surgeons are used. However, due to the expandable anchoring stent, the time on bypass is greatly reduced by the relative speed of implant in contrast to the previous time-consuming knot-tying process. As mentioned above, an exemplary hybrid prosthetic heart valve is disclosed in U.S. Pat. No. 8,641,757 to Pintor, et al., filed Jun. 23, 2011, to which priority is claimed, and which is hereby expressly incorporated by reference herein.

For definitional purposes, the terms "stent" or "anchoring stent" refer to a structural component that is capable of anchoring to tissue of a heart valve annulus. The coupling stents described herein are most typically tubular stents, or stents having varying shapes or diameters. A stent is normally formed of a biocompatible metal frame, and may be formed of a plastically-expandable material such as stainless steel or cobalt-chromium, or a self-expandable material such as Nitinol. In the context of the present invention the stents are preferably made from laser-cut tubing of a self-expandable metal. It is conceivable, however, that the coupling stent could be separate self-expanding clamps or hooks that do not define a continuous periphery. Although such devices sacrifice some contact uniformity, and speed and ease of deployment, they could be configured to work in conjunction with a particular valve member.

The term "valve member" refers to that component of a heart valve that possesses the fluid occluding surfaces to prevent blood flow in one direction while permitting it in another. As mentioned above, various constructions of valve members are available, including those with flexible leaflets and those with rigid leaflets, or even a ball and cage arrangement. The leaflets may be bioprosthetic, synthetic, metallic, or other suitable expedients. In a preferred embodiment, the non-expandable valve member is an "off-the-shelf" standard surgical valve of the type that has been successfully implanted using sutures for many years, such as the Carpentier-Edwards PERIMOUNT Magna® Aortic Heart Valve available from Edwards Lifesciences of Irvine, California, though the autonomous nature of the valve member is not absolutely required. In this sense, a "off-the-shelf" prosthetic heart valve is suitable for stand-alone sale and use, typically including a non-expandable, non-collapsible support structure having a sealing ring capable of being implanted using sutures through the sealing ring in an open-heart, surgical procedure.

As a point of further definition, the term "expandable" is used herein to refer to a component of the heart valve capable of expanding from a first, delivery diameter to a second, implantation diameter. An expandable structure, therefore, does not simply mean one that might undergo slight expansion from a rise in temperature, or other such incidental cause such as fluid dynamics acting on leaflets or commissures. Conversely, "non-expandable" should not be interpreted to mean completely rigid or dimensionally stable, as some slight expansion of conventional "non-expandable" heart valves, for example, may be observed.

An aortic valve replacement would be implanted in, or adjacent to, the aortic annulus, while a mitral valve replacement will be implanted at the mitral annulus. Certain features of the present invention are particularly advantageous for an aortic valve replacement. However, unless the combination is structurally impossible, or excluded by claim language, any of the heart valve embodiments described herein could be implanted in any body channel.

FIG. 1 shows both exploded and assembled views of an exemplary hybrid prosthetic heart valve 20 (hereinafter, "heart valve") having a valve member 22 and an expandable anchoring stent 24 with fabric coverings removed for clarity. FIG. 2 is an exploded view of the expandable anchoring stent 24 and its fabric coverings 26, 28, with the cloth-covered stent 24' seen at the bottom, while FIG. 3 shows both exploded and assembled views of the finished heart valve 20 with the fabric-covered anchoring stent 24' in its expanded, deployed state.

The exemplary hybrid prosthetic heart valve 20 of the present application desirably includes the valve member 22 with the anchoring stent 24 attached to and extending from an inflow end thereof. The valve member 22 is desirably non-collapsible and non-expandable, while the anchoring stent 24 may expand from a contracted state into the expanded state shown, as will be described. In the illustrated embodiment, the anchoring stent 24 features a series of axial struts with a chevron-shaped pattern of circumferential struts therebetween which expand when unrestrained to the shape shown in FIG. 1.

The valve member 22 preferably includes a plurality of leaflets 30 supported by and extending inward from a cloth-covered inner support frame (not shown) that defines upstanding commissure posts 32 intermediate the same number of cusps 34. There are typically three commissure posts 32 alternating with three cusps 34 to support three leaflets 30 along each of the cusps, though only two or more than three are known. The leaflets 30 provide the occluding surfaces for the prosthetic heart valve 20 which ensure one-way blood flow through the valve. The illustrated valve member 22 includes a peripheral sealing ring 36 surrounding the inflow end thereof. The heart valve 20 is desirably for implantation at the aortic annulus and the sealing ring 36 therefore preferably has an undulating up and down shape around its periphery to match the native aortic annulus.

It should be noted that a sealing ring per se may not be necessary with the present heart valve as the primary function of such a component is normally to provide a platform through which to pass a number of anchoring sutures around the valve periphery. However, sutures are not used to implant the hybrid heart valve 20 except perhaps for a small number (e.g., 3) guide sutures. For instance, several tabs extending outward from the valve structure could be used for anchoring the guide sutures which take the place of the sealing ring for that purpose. To help prevent paravalvular leaking, a peripheral seal such as a fabric skirt as described below may be added in place of the sealing ring.

The leaflets 30 are desirably flexible, preferably bioprosthetic leaflets. For example, the valve leaflets 30 may be tissue from another human heart (cadaver), a cow (bovine), a pig (porcine valve) or a horse (equine). In some embodiments, the leaflets are pericardium or treated pericardium, for example, bovine, porcine, equine, or kangaroo. Alternatively, the valve member may comprise mechanical components rather than biological tissue. Although an autonomous (e.g., capable of stand-alone surgical implant) flexible leaflet valve member 22 is described and illustrated, alternative valve members that have rigid leaflets, or are not fully autonomous may be substituted.

In one embodiment, the valve member 22 comprises a Carpentier-Edwards PERIMOUNT Magna® Aortic Heart Valve available from Edwards Lifesciences of Irvine, California. In another embodiment, the valve member 22 comprises a PERIMOUNT Magna® Aortic valve subjected to tissue treatment that permits dry packaging and sterilization, and that eliminates the need to rinse a preservative from the valves before implantation.

For bioprosthetic valves, an exemplary process includes storing the prosthetic heart valve 20 in a preservative solution after manufacture and prior to use. A preservative such as glutaraldehyde is provided within a storage jar. This "wet" storage arrangement applies to the illustrated heart valve 20 shown, which includes bioprosthetic leaflets. However, as mentioned above, the heart valve could also be used without a preservative solution for bioprosthetic leaflets that have been dried, for example, using suitable tissue treatments from Edwards Lifesciences, and also for mechanical valves.

The general function of the anchoring stent 24 is to provide the means to attach the prosthetic valve member 22 to the native aortic root. This attachment method is intended as an alternative to the present standard surgical method of suturing aortic valve bio-prostheses to the aortic valve annulus, and is accomplished in much less time. Further, this attachment method improves ease of use by eliminating most if not all suturing and knot tying. The anchoring stent 24 is formed of a self-expandable metallic member desirably covered by a polyester fabric to help seal against paravalvular leakage and promote tissue ingrowth once implanted within the annulus.

In a preferred embodiment, an inner fabric layer 26 immediately covering the anchoring stent 24 (inner fabric layer) comprises polytetrafluoroethylene (PTFE) cloth, such as TEFLON® PTFE (DuPont, Wilmington, Del.), although other biocompatible fabrics may be used. More particularly, the fabric 26 is a PTFE flat yarn. A sealing flange 28 comprises a much thicker material to provide prevention of paravalvular leakage. For instance, the sealing flange 28 is formed of a plush polymer, and made of polyethylene terephthalate (PET). More preferably, the material of the sealing flange 28 has a base yarn which is flat yarn 40/27, and a loop yarn extending therefrom made from PET 70/12 textured yarn both obtained from Atex Technologies Inc. of Pinebluff, NC. The thickness of the sealing flange 28 material is desirably about 1.2 mm, uncompressed, while the thickness of the fabric 26 may be 50% or less of that. In alternative embodiments, different materials can be used from the covering layer 26 and the sealing flange 28, such as PTFE/cloth, cloth/cloth, or PTFE or cloth for the covering layer 26 and a swellable hydrophilic polymer such as an acrylic for the sealing flange 28. The sealing flange 28 is shown located around the upper or outflow end of the anchoring stent 24, although it may also cover the entire anchoring stent or be located around just the lower or inflow end.

As seen schematically in FIGS. 1-3, the valve member 22 preferably attaches to the anchoring stent 24 via a plurality of attachment sutures 40. The sutures 40 desirably loop around an upper circumferential strut 42 on the anchoring stent 24 and pass through fabric at the inflow end of the valve member 22. There are a number of ways to connect the two components such as shown and described in U.S. Pat. No. 8,641,757 to Pintor, et al., the entire disclosure which is incorporated by reference, mentioned above.

Figures 4A, 4B:
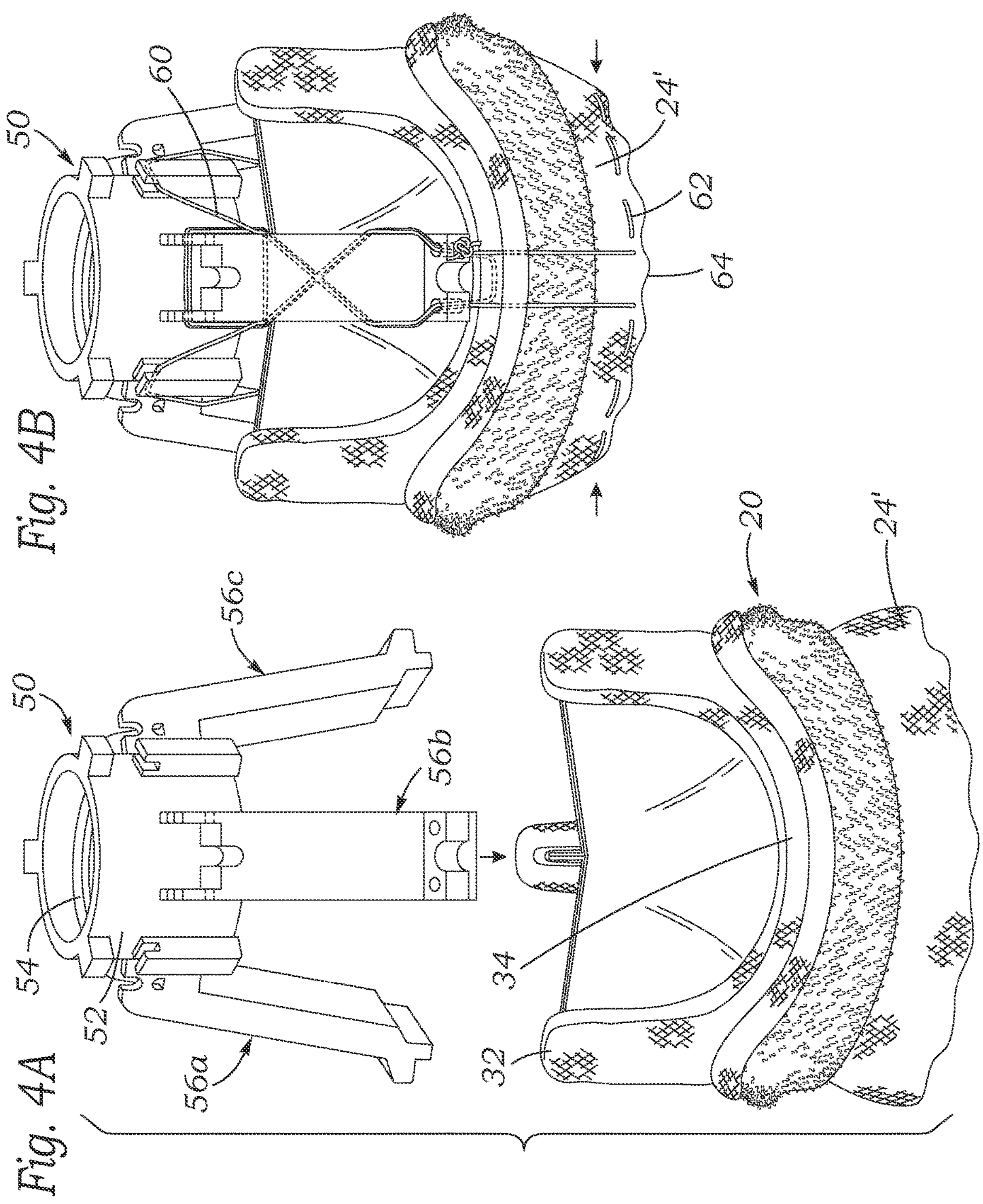
FIG. 4A is an exploded view of an exemplary valve holder above the heart valve with the anchoring stent expanded.
FIG. 4B shows the valve holder coupled to the heart valve with a pair of connecting sutures, one of which maintains the anchoring stent in its constricted, delivery state.

FIG. 4A is an exploded view of an exemplary valve holder 50 above the heart valve 20 with the fabric-covered anchoring stent 24' expanded. The valve holder 50 includes a central tubular hub 52 having internal threads 54, and a plurality of stabilizing legs 56 projecting axially and radially outward therefrom. Preferably, there are three stabilizing legs 56 each of which contacts and attaches to a cusp 34 of the valve member 22 between commissure posts 32. The valve holder 50 secures with sutures to the valve member 22 from the time of manufacture to the time of implant, as seen in FIG. 4B, and is stored with the valve member. In one embodiment, the holder 22 is formed of a rigid polymer such as polypropylene that is transparent to increase visibility of an implant procedure. The holder 22 exhibits relatively wide openings between the stabilizing legs 56, which provide a surgeon good visibility of the valve leaflets 30. The transparency of the legs further facilitates visibility and permits transmission of light therethrough to minimize or reduce shadows. It should be noted that the exemplary heart valve 20 is generally symmetric about three radial sections with three cusps, three commissures, and three flexible leaflets, matching a holder 22 with three legs 56. However, other configurations of heart valves are available and the holder may have more or fewer legs as necessary.

FIG. 4B shows the valve holder 50 coupled to the heart valve 20 with a pair of connecting sutures 60, 62, one of which maintains the anchoring stent 24' in its constricted, delivery state. As will be explained below, an upper connecting suture 60 secures each of the three legs 56 to one of the cusps 34 of the valve member 22, while a lower connecting suture 62 extends downward from one of the legs and is threaded peripherally around a lower end 64 of the anchoring stent 24'. Tension on the lower connecting suture 62 constricts the anchoring stent 24', and the suture is then tied off to maintain the anchoring stent in its delivery state, as shown.

Preferably, there is one upper connecting suture and one lower connecting suture, as shown, although only a single connecting suture or more than one of each are also possible. As will be explained, at least one suture functions to securely attach the holder to the heart valve, and one functions to maintain a self-expanding stent constricted. These functions may be accomplished with a single suture, though for the sake of stability and ease of assembly two are used, as is explained herein. Furthermore, although a particular path for both upper and lower connecting sutures are used for the particular holder shown, other suture paths can be used with other holders.

Figures 5A, 5B, 5C:
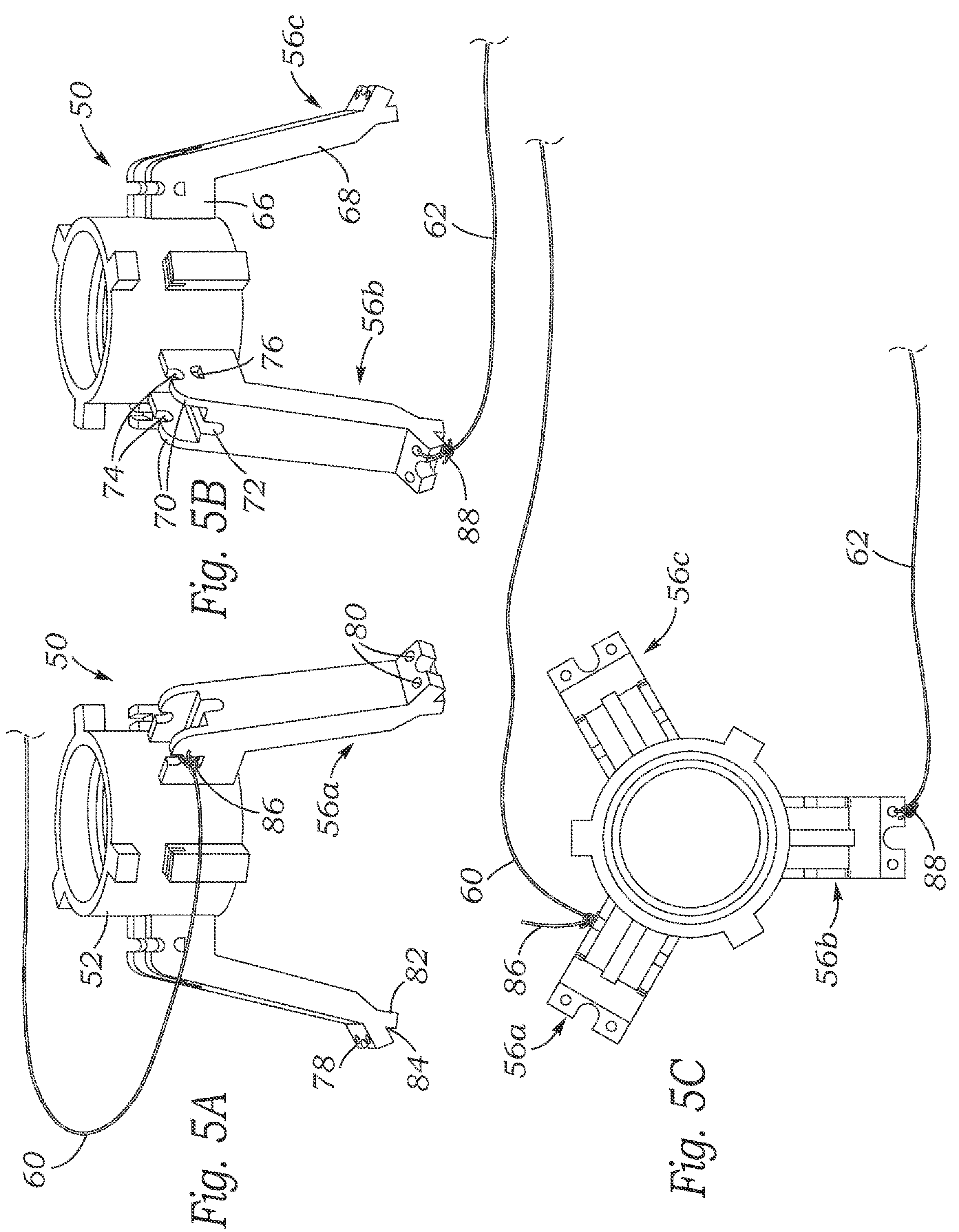
FIGS. 5A-5C are perspective and top plan views of the exemplary valve holder prior to coupling with the heart valve and showing the initial attachment locations of the first free ends of the pair of connecting sutures to the holder.

FIGS. 5A-5C best illustrate specific features of the exemplary valve holder 50. As explained above, the holder 50 preferably includes the central hub 52 and three stabilizing legs 56*a*, 56*b*, and 56*c*. For the purpose of explaining a series of steps coupling the holder 52 the prosthetic heart valve 20, the holder includes a first leg 56*a*, a second leg 56*b*, and a third leg 56*c*, moving clockwise around an axis of the holder as seen in the plan view of FIG. 5C. The connecting sutures 60, 62 are shown attached at respective first free ends to the holder prior to their use in attaching the heart valve 20. More particularly, the upper connecting suture 60 has a first end tied off on the first leg 56*a*, and the lower connecting suture 62 has a first end tied off on the second leg 56*b*.

The three legs 56*a*, 56*b*, and 56*c* are identical and evenly spaced circumferentially around the central hub 52 (e.g., 120° spacing therebetween) in the illustrated example. With reference to FIG. 5B, each leg 56 has an upper bridge portion 66 that initially projects directly radially outward from the hub 52 and a leg portion 68 that angles downward and outward. In one embodiment, the angle that each leg portion 68 makes with a central axis through the holder is between about 10°-45°. The bridge portion 66 comprises a pair of axially-oriented (e.g., vertical) outer walls 70 that are generally parallel to and extend upward over a radially-oriented cutting guide or well 72. Along the top edge of each of the outer walls 70 is formed a small notch 74 the purpose of which will become clear below. Additionally, a small aperture 76 extends through each of the outer walls 70 just below its notch 74. As seen in FIG. 5A, each leg portion 68 has a substantially rectangular cross-section on a majority of its length as it extends downward from the bridge portion 66, though other cross-sections are contemplated. A lower end of each leg portion 68 terminates in an outwardly-angled flange 78 defining a pair of through holes 80, and a downwardly-directed flange 82. A channel 84 formed between the flange 78, 82 receives a portion of the cusps 34 of the valve member 22, as will be seen. The downwardly-directed flange 82 may be eliminated such that only the outwardly-angled flanges 78 contact the valve cusps 34. Two through holes 80 open on their lower ends in the channel 84.

The upper connecting suture 60 has a first free end 86 that is tied to one of the outer walls 70 of the first holder leg 56*a*, as best seen in FIG. 5A. Specifically, the first free end 86 loops through the small aperture 76 and over the notch 74 right above it, and is tied off with a knot. The upper connecting suture 60 is connected to a left-hand one of the two outer walls 70, as looking radially inward at the first leg 56*a*. The lower connecting suture 62 has a first free end 88 tied to the outwardly-angled flange 78 in the second holder leg 56*b*, as best seen in FIG. 5B (and also FIG. 15A). In particular, the first free end 88 loops through a right-hand one of the through holes 80 in the flange 78 and is tied off with a knot. As will be explained below, both of the connecting sutures 60, 62 are respectively threaded down through the heart valve 20 and around various features on the holder 50, and ultimately a second free end is tied at the same location as the first free and. In this regard each of the connecting sutures 60, 62 is secured at both its free ends to the holder 50 and has a middle portion in between.

Figures 6, 7A, 7B, 8A, 8B:
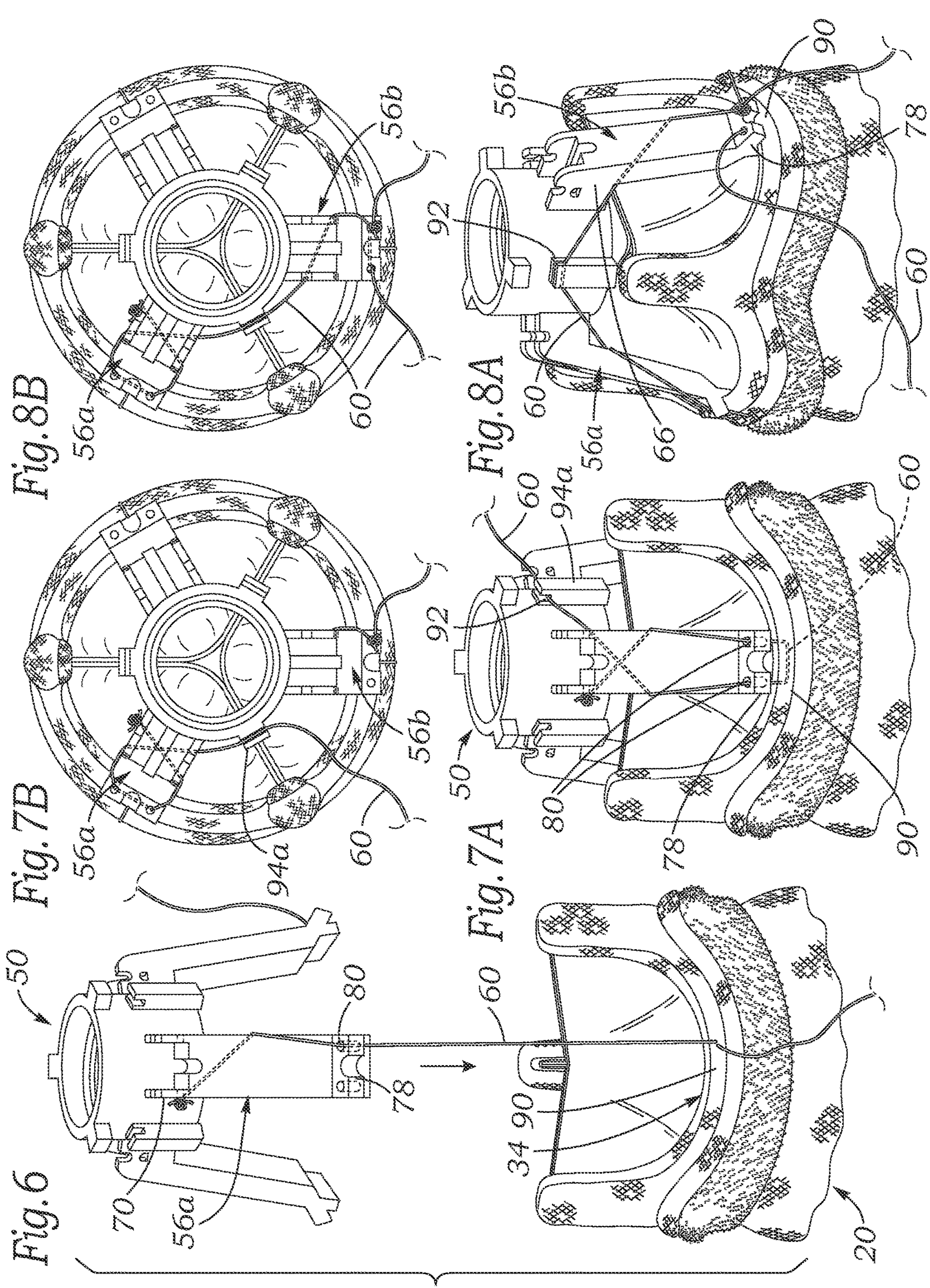

FIGS. 6-11 illustrate a number of steps that an assembler takes to couple the valve holder 50 to the heart valve 20 using the upper connecting suture 60. Initially, FIG. 6 shows the valve holder 50 exploded above the heart valve 20 with the first leg 56*a* facing out from the page. In each of the succeeding drawings (e.g., FIGS. 7A-11B), the holder 50 abuts the valve 20 and the suture 60 is shown progressively securing them together. It should be noted that the assembly rotates in the elevational "A" series of views for clarity, while it remains stationary as looking from above in the "B" series of views.

As explained above, the suture 60 is first tied off at a left hand one of the vertical outer walls 70 on the first leg 56*a*. From there, as seen in FIGS. 7A and 7B, the assembler passes the suture 60 to the inside of the first leg 56*a,* crossing over from the left side to the right side, and then emerging to the outside of the leg and extending downward through one of the through holes 80 in the outwardly-angled flange 78. The suture 60 continues downward and is threaded through a fabric portion of the heart valve 20. More particularly, the valve member 22 has fabric edge 90 that defines a portion of the fabric-covered support frame. The assembler threads the suture 60 through this fabric edge 90 at the cusps 34 of the valve member 22. Each leg 56 contacts and is secured to a mid-portion of each of the cusps 34 of the valve member 22. As will be explained, each suture 60 passes downward through the first through hole 80 in the flange 78, through the fabric edge 90, and back up through the second through hole 80, as seen in FIG. 7A.

FIGS. 7A and 7B illustrate the next step of threading the upper connecting suture 60 around the valve holder 50. After passing down and back up through the holes 80 in the flange 78 of the first leg 56*a,* and through the fabric edge 90, the assembler wraps the suture 60 around the left side of the first leg and around the inside thereof, crossing over the first length of the suture to exit on the right side of the leg, as shown. From there, the assembler passes the suture 60 in a counterclockwise manner (looking from above) around the cylindrical hub 52 and through an upwardly-opening notch 92 provided in a first rail 94*a* that extends outward from the hub between the first and second legs 56*a,* 56*b.*

Now with reference to FIGS. 8A and 8B, the suture 60 angles downward from the notch 92 and passes underneath the upper bridge portion 66 of the second holder leg 56*b.* The suture 60 wraps around the inside of the second leg 56*b,* and emerges to the front thereof. The suture 60 is then is then passed downward through the right-hand hole 80 of the flange 78, through the fabric edge 90 of the valve 20, and back up through the left-hand hole. At this point, the upper connecting suture 60 has secured both the first and second legs 56*a,* 56*b* to the valve 20, and is shown dangling loose; however, in practice the assembler typically maintains some tension on the suture.

Figures 9A, 9B, 10A, 10B, 11A, 11B:
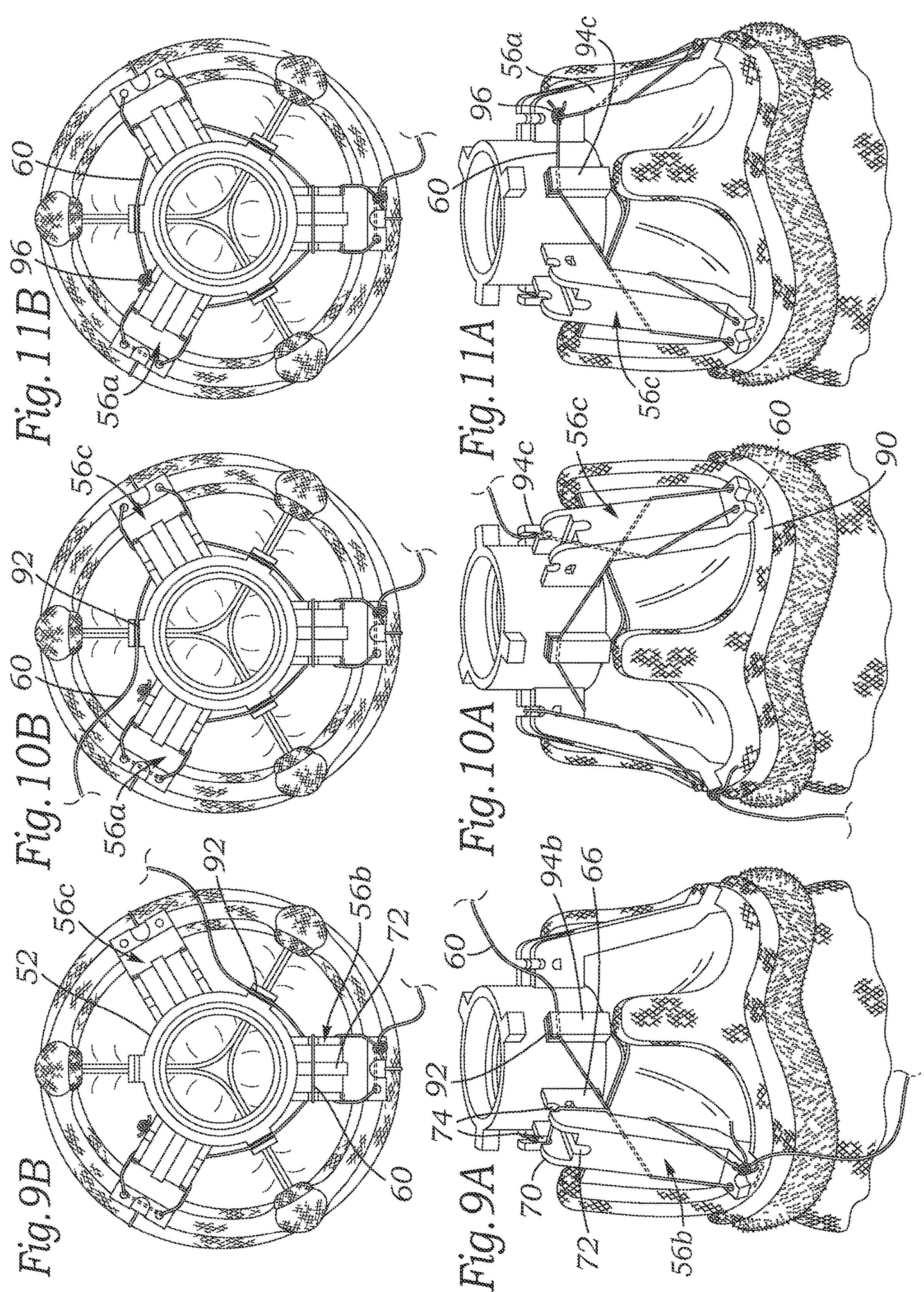

In the next step, as seen in FIGS. 9A and 9B, the assembler brings the upper connecting suture 60 around the inside of the second leg 56*b,* crossing over the strand of the suture that previously passed to the inside of the leg. He or she then loops the suture 60 counterclockwise once over the upper bridge portion 66, making sure that the suture passes through both of the notches 74 in the outer walls 70. In this way, the suture crosses over the cutting well 72 defined between the outer walls 70 in the second leg 56*b*. The connecting suture 60 is looped underneath the bridge portion 66 and again continues in a counterclockwise fashion around the hub 52 and is positioned in the notch 92 of a second rail 94*b* between the second and third legs 56*b,* 56*c.*

Next, as seen in FIGS. 10A and 10B, the assembler wraps the suture 60 behind or to the inside of the third leg 56*c,* and around the outside of the leg and passes it downward through the right-hand hole 80 in the flange 78. As before, the suture 60 passes downward through the fabric edge 90 of the valve 20 and upward through the left-hand hole 80, thus securing the third leg 94*c* to the valve 20. As with the other two legs, the assembler then wraps the suture 60 around the left side and to the inside of the third leg 56*c,* and angles it in a counterclockwise direction over the notch 92 of a third rail 94*c* between the third and first legs 56*c,* 56*a.*

Figures 15A, 15B, 15C:
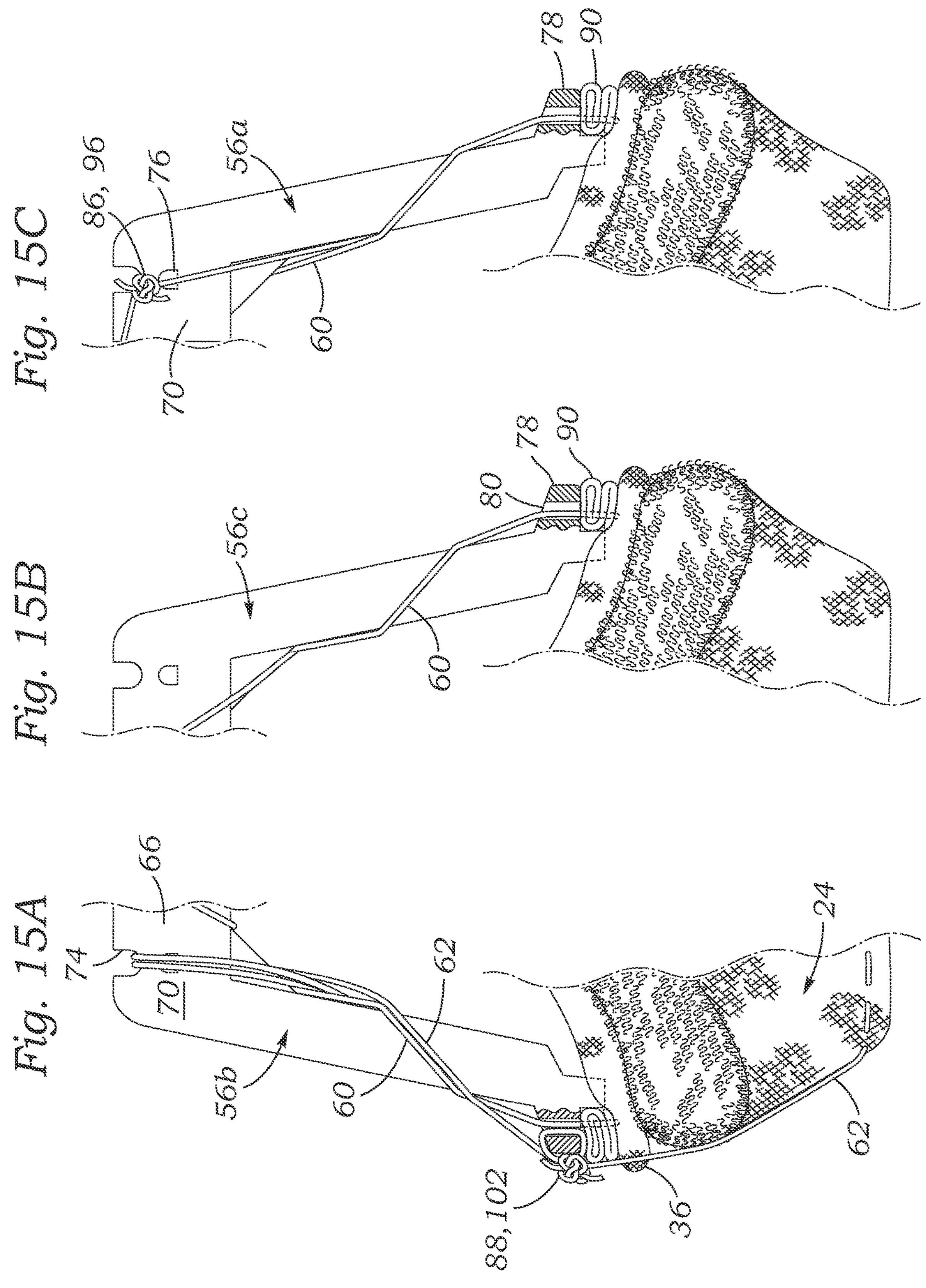
FIGS. 15A-15C are several partial sectional elevational views of the three valve holder legs having the connecting sutures attached thereto.

FIGS. 11A and 11B show the upper connecting suture 60 as it extends from the third rail 94*c* to the first leg 56*a* and its second free end 96 is tied off at a knot (also seen in FIG. 15C). The knot is tied off at the small aperture 76 on one of the outer walls 70 of the first leg 56*a,* along with the first free end 86 of the connecting suture 60, as was shown in FIGS. 5A and 5B. In the final assembly, there is a single connecting suture 60 wrapped around the holder 50 and securing the three legs 56 at the three cusps 34 of the valve 20. Further, a single-cut release point is provided where the suture 60 wraps around the bridge portion 66 and over the cutting well 72 on the second leg 56*b.* Since the two free ends 86, 96 of the suture 60 tie off on the holder, severing the middle portion at the cutting well 72 permits the holder 50 to be pulled free of the valve 20, with the suture 60 relatively easily sliding through out of the fabric edges 90.

Once the upper connecting suture 60 secures the holder 50 to the heart valve 20, the lower connecting suture 62 is attached and the anchoring stent 24 constricted, as will be explained with reference to FIGS. 12-13. However, it should be noted that the configuration shown in FIGS. 11A and 11B wherein a single connecting suture 60 attaches the holder 50 to the valve 20 at three cusp locations and features a single-cut release can be used for valves other than the exemplary embodiment. That is, the valve 20 may include an anchoring stent that is plastically expandable as opposed to being self-expandable. For instance, the valves shown in U.S. Pat. No. 8,641,757 to Pintor, et al. have balloon expandable anchoring stents, and the holder 50 and upper connecting suture 60 configuration disclosed herein could be used to manipulate those valves. In that case, a lower connecting suture could be omitted, as its purpose is to constrict a self-expandable anchor stent. It should also be noted that the valve may not have an anchor stent at all, and the holder 50 and upper connecting suture 60 configuration disclosed herein could be used to manipulate "standard" as opposed to "hybrid" prosthetic heart valves.

Figures 12A, 12B:
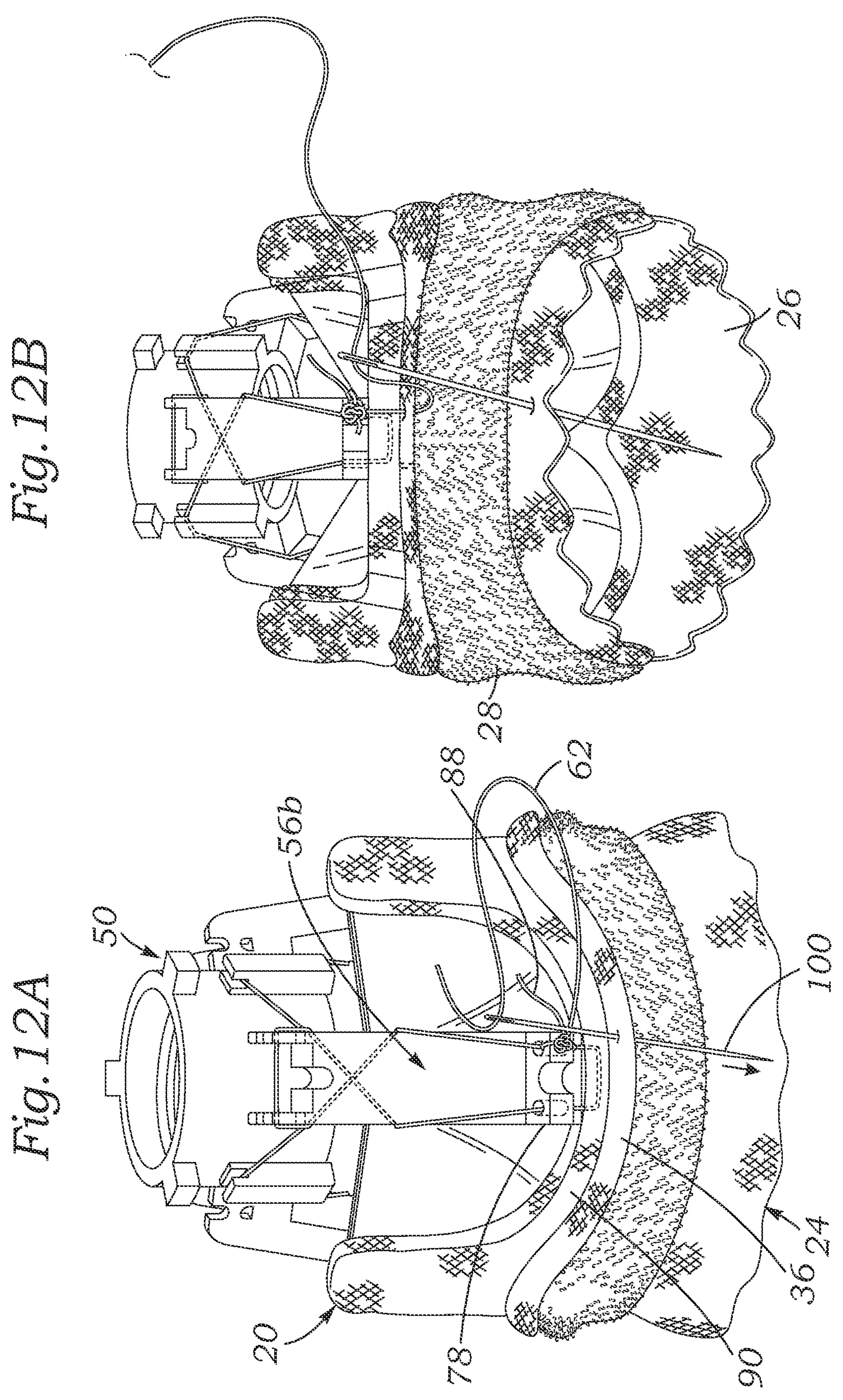

With reference to FIGS. 12A and 12B an initial path of the lower connecting suture 62 is shown. The reader will recall that the first free end 88 is tied to the outwardly-angled flange 78 in the second holder leg 56*b,* as seen in FIG. 5B. The assembler uses a needle 100 to thread the suture 62 downward through the peripheral sealing ring 36 of the heart valve 20, which is just outside the fabric edge 90 that defines a portion of the fabric-covered support frame. The suture 62 continues to the outside of the valve 20 and threads through a portion of the fabric at a lower end of the anchoring stent 24. In the illustrated embodiment, the needle 100 and suture 62 pass through the fabric layer 26 immediately covering the anchoring stent 24 (inner fabric layer), although it may also be that the sealing flange 28 extends or covers the lower end of the stent. In any event, the path of the suture 62 is substantially straight down from the sealing ring 36 to the lower edge of the fabric-covered stent 24.

Figures 12C, 12D:
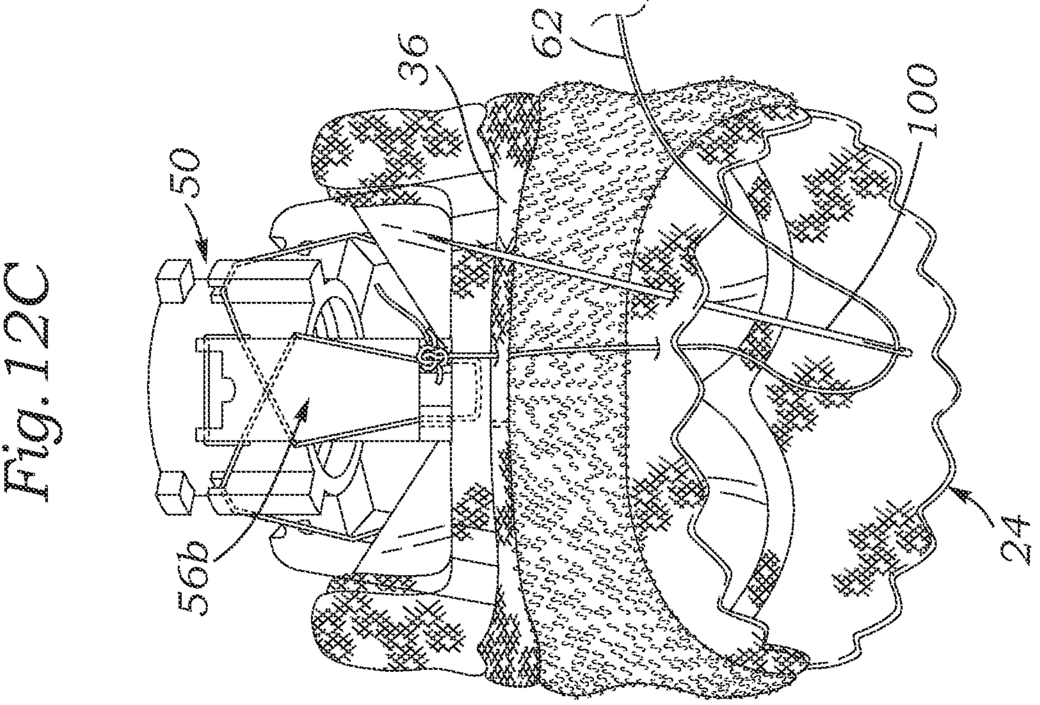
FIGS. 12C and 12D illustrate the path of the lower connecting suture as it circumscribes the lower end of the anchoring stent and passes back upward to the second leg of the valve holder.

FIGS. 12C and 12D illustrate the lower connecting suture 62 being sewn around the lower end of the anchoring stent 24 (through the fabric covering). The assembler uses the needle 100 to thread the suture 62 in and out of the stent 24 in a serpentine fashion, around the periphery thereof, it comes full circle adjacent to the starting point below the second leg 56*b.* Prior to this threading step, the stent 24 has been constricted by an external force, such as with a separate cinch or fixture (not shown) that encircles the lower end of the stent and forces it inward. The suture 62 emerges to the outside of the stent 24 and passes directly upward to the left-hand hole 80 of the flange 78 in the second leg 56*b,* again passing through the sealing ring 36. At this stage the anchoring stent 24 remains in an expanded configuration, flared slightly outwardly.

Figure 12F:
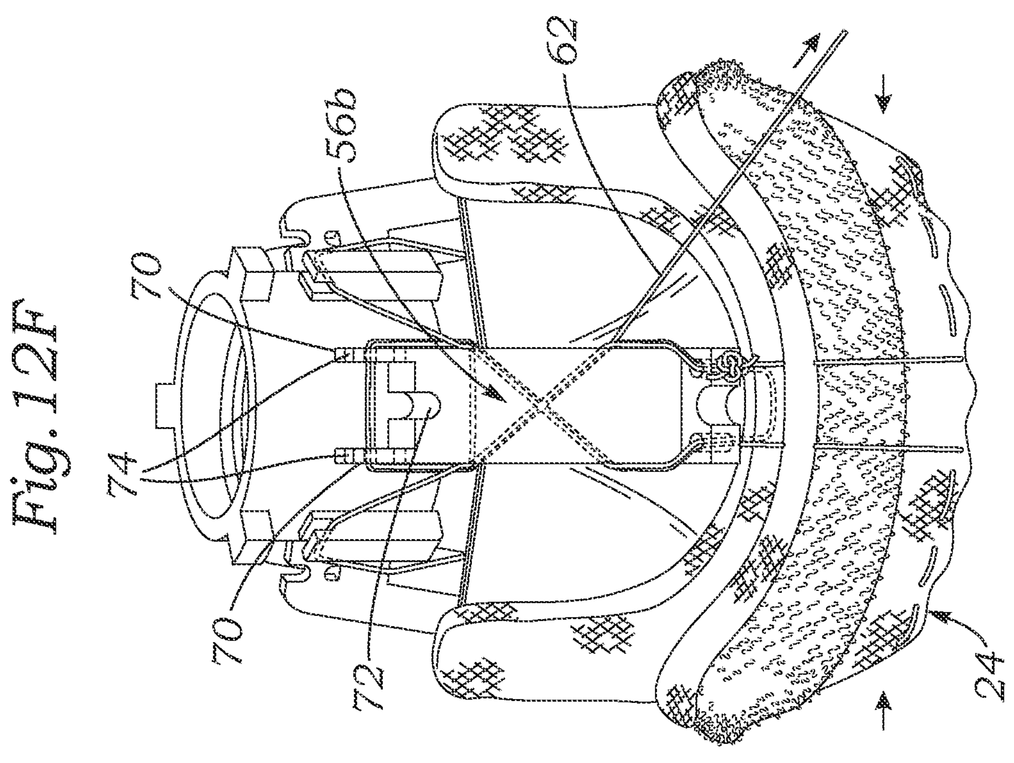
FIG. 12F illustrates conversion of the anchoring stent from its expanded to its constricted state by tensioning the lower connecting suture.
Figure 12E:
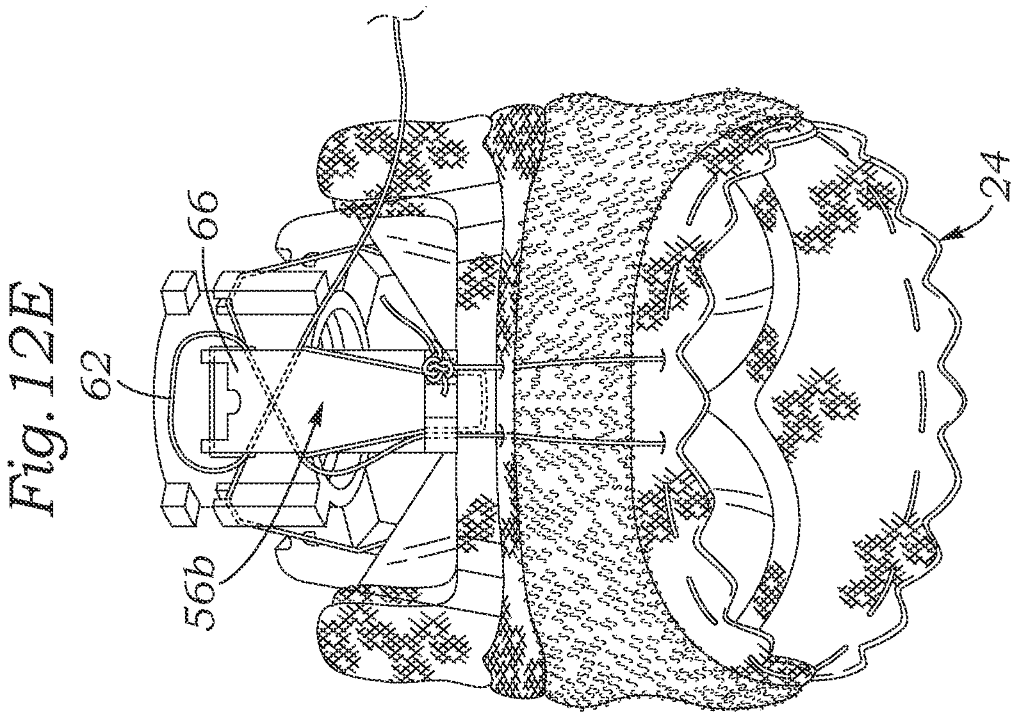
FIG. 12E illustrates the path of the lower connecting suture as it wraps around the cutting well provided on the second leg of the holder.

Now with reference to FIGS. 12E and 12F, the lower connecting suture 62 circles behind or to the inside of the second leg 56*b,* and then wraps around the upper bridge portion 66 thereof, through both of the notches 74 in the outer walls 70. In this way, both the upper and lower connecting sutures 60, 62 traverse the cutting well 72 on the same leg 56*b*. FIG. 12F illustrates the free end of the connecting suture 62 again being passed behind or to the inside of the second leg 56*a*.

Figures 13A, 13B:
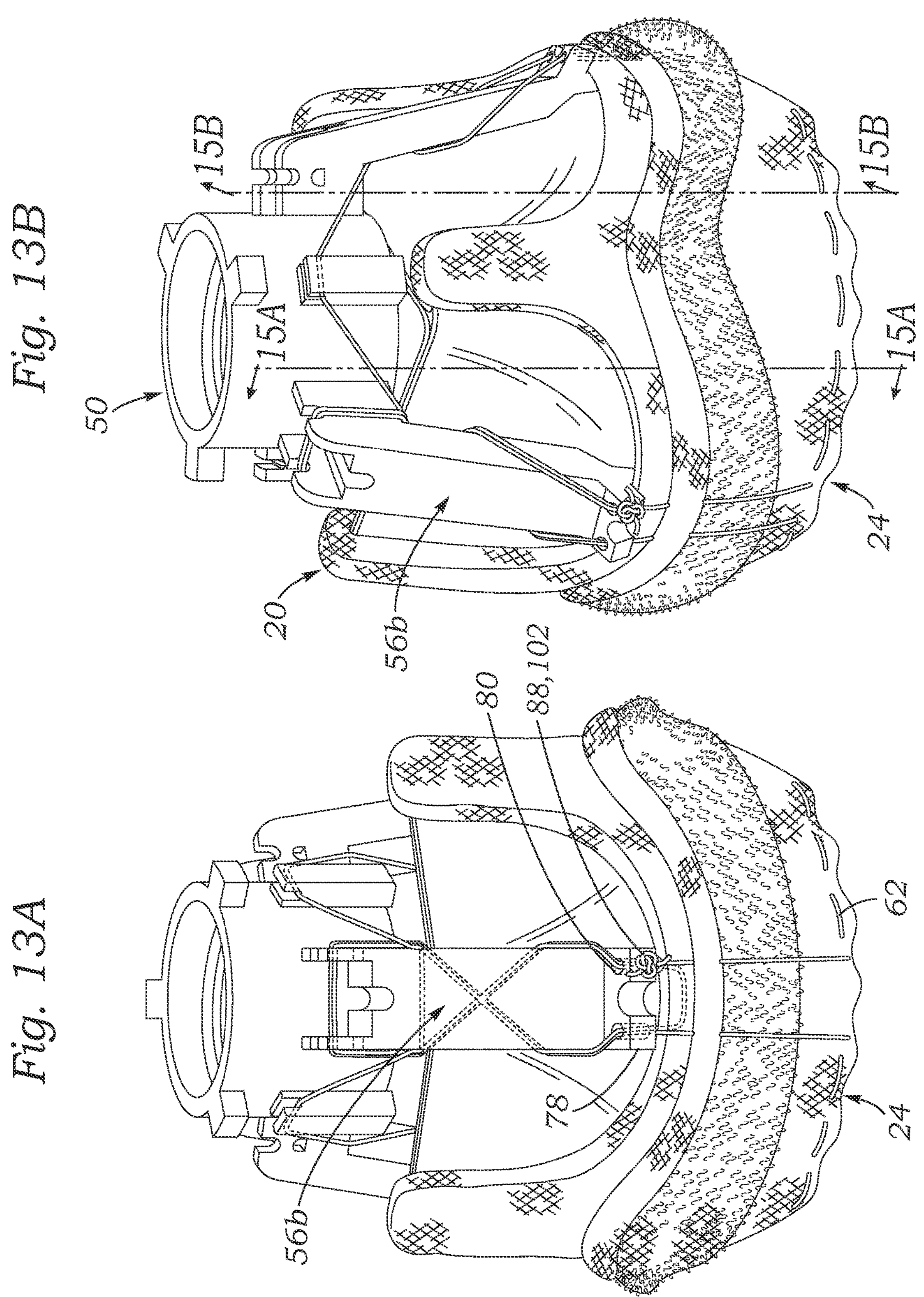

Finally, with reference to FIGS. 13A and 13B, a second free end 102 thereof is again secured to the right-hand hole 80 in the outwardly-angled flange 78 in the second leg 56*b*. Both the first and second free ends 88, 102 are thus secured to the holder at the same location. Some tension will be applied to the lower connecting suture 62 before securing it in this manner so that it can maintain the stent 24 in its constricted state without allowing any recoil. The external fixture (not shown) used to constrict the stent 24 can then be removed.

Figures 14A, 14B:
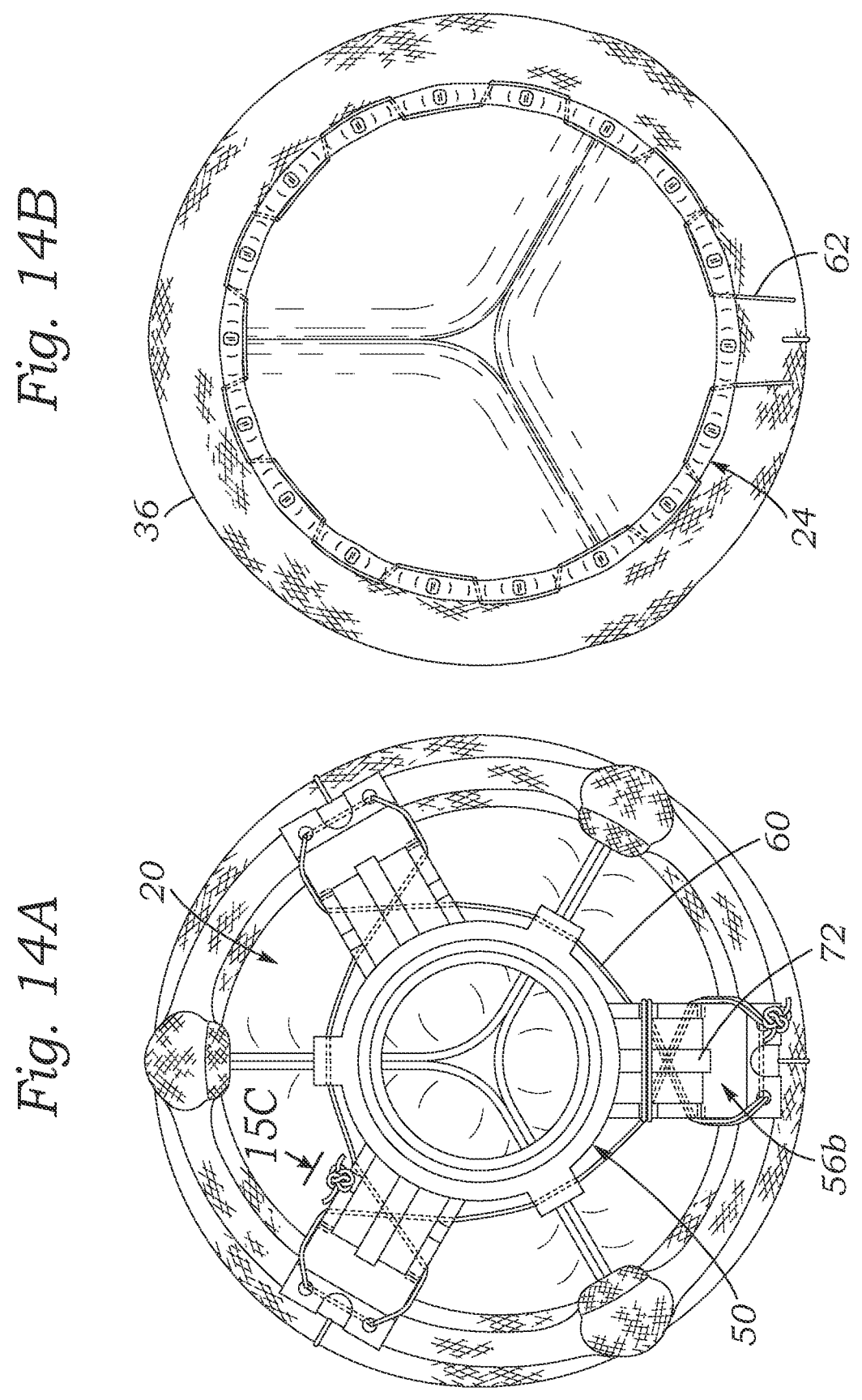

FIGS. 14A and 14B are top and bottom plan views, respectively, of the valve holder 50 secured to the heart valve 20 using the connecting sutures 60, 62. The release of the holder 50 from the valve 20 and conversion of the anchoring stent 24 from its contracted to its expanded states are enabled by severing the sutures 60, 62 at the cutting well 72 in the second leg 56*b,* in a single-point release configuration. The in-and-out or serpentine weave of the lower connecting suture 62 through the stent 24 is seen in FIG. 14B.

FIGS. 15A-15C are several partial sectional elevational views of the three valve holder 50 legs further illustrating the connecting sutures attached thereto. The second leg 56*b* is seen from one side in FIG. 15A to show the knot at which the first and second free ends 88, 102 of the lower connecting suture 62 attach. The downward path of the lower connecting suture 62 through the sealing ring 36 and to the lower end of the stent 24 is also seen. FIG. 15A also shows the two sutures 60, 62 wrapping around the upper bridge portion 66 and through both of the notches 74 in the outer walls 70 of the second leg 56*b*. As mentioned, both the upper and lower connecting sutures 60, 62 therefore traverse the cutting well 72 on the second leg 56*b*. FIG. 15B shows the third leg 56*c* from its left side, illustrating the upper connecting suture 60 passing downward around the leg and through the holes 80 in the flange 78 so as to be secured to the fabric edge 90 at the valve cusps 34. Finally, FIG. 15C shows the first and second free ends 86, 96 of the upper connecting suture 60 tied off at the small aperture 76 on one of the outer walls 70 of the first leg 56*a*. Again, the suture 60 wraps around the leg and passes down through the flange 78 to secure at the fabric edge 90 of the valve 20.

Figures 16A, 16B:
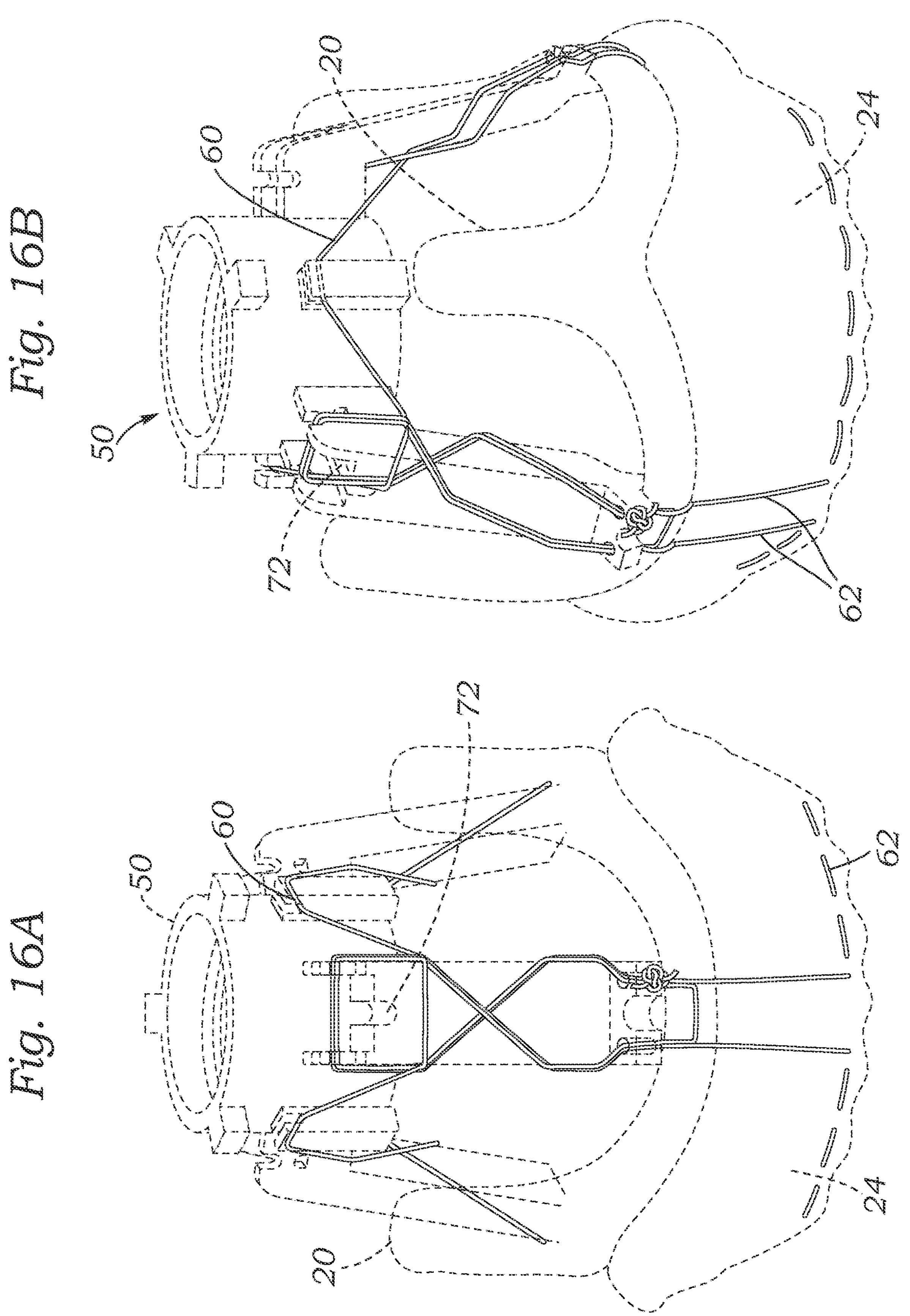
FIGS. 16A and 16B are perspective views at two different angles of the valve holder and heart valve assembly shown in phantom so as to better illustrate the pathway of the connecting sutures.

FIGS. 16A and 16B are perspective views at two different angles of the valve holder 50 and heart valve 20 assembly shown in phantom so as to better illustrate the pathway of the connecting sutures 60, 62. These views more clearly illustrate how the upper connecting suture 60 encircles the holder 50, while the lower connecting suture 62 encircles the lower end of the stent 24, and both converge at the single cutting well 72 for a one-cut release of both the holder and stent.

Figures 17A, 17B:
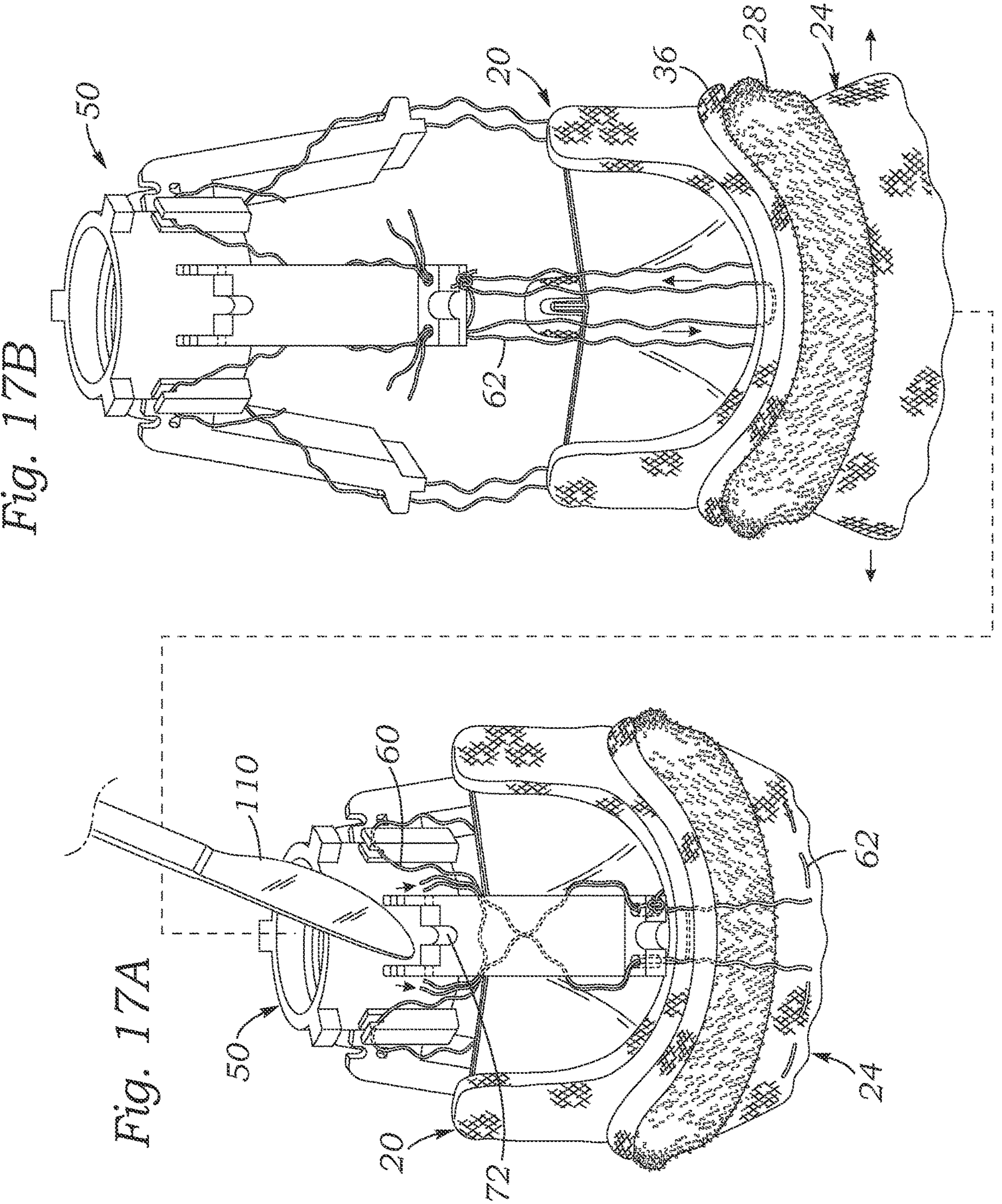
FIG. 17A illustrates a scalpel descending into the cutting well on the second leg of the valve holder to sever the two connecting sutures.
FIG. 17B shows the consequent conversion of the anchoring stent from its constricted to its expanded state and separation of the valve holder from the heart valve.

FIG. 17A illustrates a scalpel 110 descending into the cutting well 72 on the second leg 56*b* of the valve holder 50. This action severs the two connecting sutures 60, 62, thus disengaging the holder 50 from the valve 20 and allowing the anchoring stent 24 to expand. FIG. 17B shows the conversion of the anchoring stent 24 from its constricted to its expanded state and separation of the valve holder 50 from the heart valve 20. This operation will occur after the valve 20 has been seated at the target annulus. If this is the aortic annulus, conversion of the stent 24 causes it to expand outward into contact with the subvalvular structure just below the annulus. The sealing ring 36 and to an extent the sealing flange 28 contact the upper side of the aortic annulus, and thus the valve 20 is held in place. Additional sutures or clips may also be used.

Figures 18A, 18B:
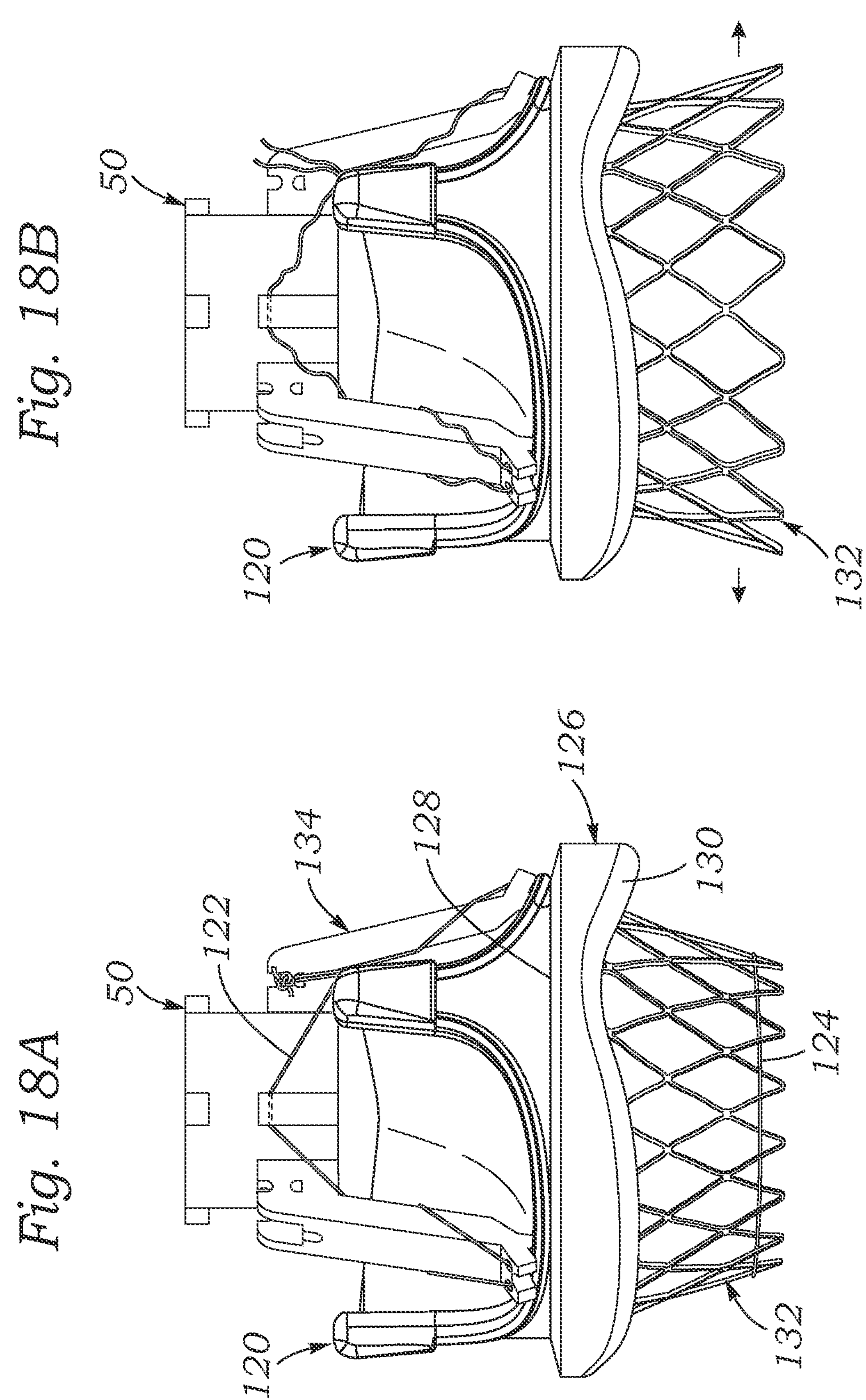
FIG. 18A is an elevational view of the valve holder secured to an alternative hybrid prosthetic heart valve using connecting sutures.
FIG. 18B is an elevational view of the assembly of FIG. 18A after severing of the connecting sutures to permit an anchoring stent of the heart valve to expand.

FIG. 18A is an elevational view of the valve holder 50 secured to an alternative hybrid prosthetic heart valve 120 using connecting sutures 122, 124. The heart valve 120 is substantially the same as described above, though a sealing ring 126 has a substantially planar upper face 128 and an undulating lower face 130 that matches the aortic annulus. Also, an anchoring stent 132 (shown without fabric covering for clarity) is modified from that shown above at 24 in FIGS. 1-2. Namely, rather than a series of axial struts with a chevron-shaped pattern of circumferential struts therebetween, as before, the stent 132 has a series of crossed struts that define a regular array of diamond-shaped cells therebetween.

As described above, an upper connecting suture 122 secures three legs 134 of the holder 50 to cusps of the valve 120. A lower connecting suture 124 attaches to the holder (not shown) passes downward to a lower end of the stent 132, and encircles and constricts the lower end when under tension. Both connecting sutures 122, 124 preferably pass over a single cutting well on the holder to enable simultaneous severing thereof and detachment of the holder and expansion of the stent 132, as seen in FIG. 18B.

While the certain embodiments are described and illustrated herein, it is to be understood that the words and drawings that have been used are words of description and not of limitation. Therefore, changes may be made within the appended claims without departing from the true scope of the disclosure.

What is claimed is:

1. A system for delivering a prosthetic heart valve to a native valve annulus, comprising:

a prosthetic heart valve including an annular support structure and a self-expandable anchoring stent together defining a flow orifice and an inflow end defining an inflow direction with an outflow direction opposite thereto, the self-expandable anchoring stent comprising a first end and a second end, the prosthetic heart valve having valve leaflets attached to the support structure and mounted to alternately open and close across the flow orifice;

a valve holder having a structure adapted to mate with a delivery handle; and a connecting suture tied at first and second free ends to the valve holder and attaching the valve holder to the prosthetic heart valve at multiple locations, the connecting suture being routed over a single cutting well on the valve holder such that severing the connecting suture at the single cutting well detaches the valve holder from the prosthetic heart valve, the connecting suture extending around the anchoring stent in tension and constricting the second end of the self-expandable anchoring stent to a contracted state for delivery to the native valve annulus.

2. The system of claim 1, wherein the support structure is covered by a fabric and the valve holder has three legs that contact the fabric-covered support structure at three locations, and wherein the connecting suture passes circumferentially around the valve holder and threads through the fabric at the three locations.

3. The system of claim 2, wherein the support structure has three commissure posts projecting in the outflow direction and three cusps therebetween that arc in the inflow direction, wherein the three legs angle outward and in the inflow direction from a central hub of the valve holder to a terminal foot on each leg that contacts the prosthetic heart valve at one of the three cusps, and wherein the connecting suture is tied at the first and second free ends to the holder and in between passes circumferentially around the central hub of the holder and descends down each of the three legs to pass through the fabric at each of the three cusps.

4. The system of claim 3, wherein the connecting suture passes through two holes at the terminal foot of each of the three legs and threads through the fabric at each of the three cusps between the two holes, and wherein the connecting suture circles completely around each of the three legs between the hub and its respective terminal foot.

5. The system of claim 3, wherein the connecting suture is tied at the first and second free ends to one of the three legs of the holder.

6. The system of claim 1, wherein the self-expandable anchoring stent has the first end extending around the flow orifice and mounted to the prosthetic heart valve at an inflow end of the support structure, the anchoring stent having the second end projecting in the inflow direction away from the support structure, the second end transitioning between the contracted state and an expanded state.

7. The system of claim 6, wherein the connecting suture extends around the second end of the anchoring stent in tension and constricts the second end to the contracted state.

8. The system of claim 7, wherein the support structure is fabric-covered and further including an upper connecting suture tied at two free ends to the valve holder and passing through the fabric-covered support structure, wherein the connecting suture and the upper connecting suture pass over the single cutting well on the valve holder such that severing the connecting suture and the upper connecting suture both releases tension in the connecting suture to permit the second end to expand toward the expanded state and detaches the valve holder from the prosthetic heart valve.

9. The system of claim 7, wherein the anchoring stent has a fabric covering, and wherein the connecting suture passes through the fabric covering around the anchoring stent.

10. The system of claim 7, wherein the support structure has three commissure posts projecting in the outflow direction and three cusps therebetween that arc in the inflow direction, wherein the valve holder has three legs that angle outward and in the inflow direction from the central hub to contact the support structure at the three cusps, and wherein the connecting suture is tied at the first and second free ends to a terminal foot of one of the three legs.

11. The system of claim 1, wherein the support structure is non-expandable and non-collapsible.

* * * * *